United States Patent
Seo et al.

(10) Patent No.: US 10,315,308 B2
(45) Date of Patent: *Jun. 11, 2019

(54) METHOD AND APPARATUS FOR CALCULATING TORQUE OF WALKING ASSISTANCE DEVICE

(71) Applicant: Samsung Electronics Co., Ltd., Suwon-si, Gyeonggi-do (KR)

(72) Inventors: Keehong Seo, Seoul (KR); Jusuk Lee, Hwaseong-si (KR); Bokman Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/818,038

(22) Filed: Nov. 20, 2017

(65) Prior Publication Data

US 2018/0071910 A1   Mar. 15, 2018

Related U.S. Application Data

(63) Continuation of application No. 15/000,638, filed on Jan. 19, 2016, now Pat. No. 9,868,204.

(30) Foreign Application Priority Data

Aug. 11, 2015   (KR) .................. 10-2015-0113226

(51) Int. Cl.
*B25J 9/00* (2006.01)
*A61H 3/00* (2006.01)
(Continued)

(52) U.S. Cl.
CPC ............. *B25J 9/0006* (2013.01); *A61B 5/112* (2013.01); *A61H 1/0244* (2013.01); *A61H 3/00* (2013.01);
(Continued)

(58) Field of Classification Search
USPC .......... 700/245–264; 601/34, 35; 623/24–27, 623/32, 39; 901/1, 46
See application file for complete search history.

(56) References Cited

U.S. PATENT DOCUMENTS 4,697,808 A * 10/1987 Larson .................. A61F 5/0102
482/4
8,298,164 B2 * 10/2012 Yasuhara ............. A61H 1/0244
482/66
(Continued)

FOREIGN PATENT DOCUMENTS

EP   2796123 A1   10/2014
JP   2007061527 A   3/2007
(Continued)

OTHER PUBLICATIONS

Knaepen, Kristel et al., "Human-Robot Interaction: Kinematics and Muscle Activity Inside a Powered Compliant Knee Exoskel", IEEE Transactions on Neural Systems and Rehabilitation Engineering, IEEE Service Center, New York, NY, vol. 22, No. 6, Nov. 1, 2014, pp. 1128-1137, XP011564477.

(Continued)

*Primary Examiner* — Jonathan L Sample
(74) *Attorney, Agent, or Firm* — Harness, Dickey & Pierce, P.L.C.

(57) ABSTRACT

A method and apparatus for calculating a torque of a walking assistance device, the method including receiving a measured joint angle, obtaining a gait parameter with respect to a transition among a predetermined number of gait states based on the joint angle, obtaining a gait cycle based on the joint angle, and obtaining an output torque based on the gait cycle and the gait parameter, is provided.

20 Claims, 17 Drawing Sheets

(51) Int. Cl.
  *A61B 5/11*   (2006.01)
  *G05B 19/042*  (2006.01)
  *A61H 1/02*   (2006.01)

(52) U.S. Cl.
  CPC .... *G05B 19/042* (2013.01); *A61H 2201/1215* (2013.01); *A61H 2201/164* (2013.01); *A61H 2201/165* (2013.01); *A61H 2201/1628* (2013.01); *A61H 2201/501* (2013.01); *A61H 2201/5061* (2013.01); *A61H 2201/5064* (2013.01); *A61H 2201/5069* (2013.01); *A61H 2201/5079* (2013.01); *A61H 2201/5084* (2013.01); *A61H 2201/5097* (2013.01); *A61H 2230/085* (2013.01); *A61H 2230/605* (2013.01); *A61H 2230/625* (2013.01); *G05B 2219/36435* (2013.01); *G05B 2219/40305* (2013.01); *Y10S 901/09* (2013.01)

(56) References Cited

U.S. PATENT DOCUMENTS

| | | | | |
|---|---|---|---|---|
| 9,610,209 | B2* | 4/2017 | Yasuhara | A61H 3/00 |
| 9,662,526 | B2* | 5/2017 | Agrawal | A61H 1/0266 |
| 9,687,377 | B2* | 6/2017 | Han | A61F 5/0125 |
| 2004/0044440 | A1* | 3/2004 | Takenaka | B62D 57/032 |
| | | | | 700/245 |
| 2004/0148268 | A1* | 7/2004 | Reil | B25J 9/161 |
| | | | | 700/247 |
| 2005/0251079 | A1* | 11/2005 | Carvey | A61F 5/0102 |
| | | | | 602/26 |
| 2007/0123997 | A1* | 5/2007 | Herr | A61F 2/60 |
| | | | | 623/27 |
| 2009/0055019 | A1* | 2/2009 | Stiehl | B25J 9/1671 |
| | | | | 700/249 |
| 2010/0132464 | A1* | 6/2010 | Yasuhara | A61B 5/1038 |
| | | | | 73/504.12 |
| 2011/0288453 | A1* | 11/2011 | Endo | A61H 1/0244 |
| | | | | 601/35 |
| 2012/0016278 | A1* | 1/2012 | Nakashima | A61H 1/024 |
| | | | | 601/34 |
| 2012/0215140 | A1* | 8/2012 | Hirata | A61H 1/0244 |
| | | | | 601/35 |
| 2012/0226203 | A1* | 9/2012 | Nakashima | A61H 3/00 |
| | | | | 601/34 |
| 2012/0259431 | A1* | 10/2012 | Han | A61F 5/0125 |
| | | | | 623/24 |
| 2012/0310122 | A1* | 12/2012 | Endo | A61H 1/0244 |
| | | | | 601/35 |
| 2013/0056981 | A1* | 3/2013 | Mullins | F03G 5/06 |
| | | | | 290/7 |
| 2013/0116820 | A1* | 5/2013 | Lee | B62D 57/032 |
| | | | | 700/254 |
| 2013/0158445 | A1* | 6/2013 | Kazerooni | A61H 3/00 |
| | | | | 601/35 |
| 2013/0197408 | A1* | 8/2013 | Goldfarb | A61F 5/0102 |
| | | | | 601/35 |
| 2013/0226048 | A1* | 8/2013 | Unluhisarcikli | A61H 3/00 |
| | | | | 601/34 |
| 2013/0310979 | A1* | 11/2013 | Herr | B62D 57/032 |
| | | | | 700/258 |
| 2014/0142475 | A1* | 5/2014 | Goldfarb | A61H 3/00 |
| | | | | 601/35 |
| 2014/0276304 | A1* | 9/2014 | Dollar | A61F 5/0102 |
| | | | | 602/16 |
| 2014/0277739 | A1* | 9/2014 | Kornbluh | B25J 9/0006 |
| | | | | 700/260 |
| 2015/0120044 | A1* | 4/2015 | Cory | B62D 57/032 |
| | | | | 700/250 |
| 2015/0173993 | A1* | 6/2015 | Walsh | A61H 1/024 |
| | | | | 414/4 |
| 2015/0182408 | A1* | 7/2015 | Roh | A61H 3/00 |
| | | | | 482/51 |
| 2015/0190923 | A1* | 7/2015 | Seo | B25J 9/0006 |
| | | | | 602/16 |
| 2015/0297934 | A1* | 10/2015 | Agrawal | A61H 1/0266 |
| | | | | 482/4 |
| 2015/0366738 | A1* | 12/2015 | Endo | A61H 3/00 |
| | | | | 482/4 |
| 2015/0366739 | A1* | 12/2015 | Endo | A61H 3/00 |
| | | | | 482/4 |
| 2016/0067061 | A1* | 3/2016 | Nagarajan | B25J 9/0006 |
| | | | | 623/24 |
| 2016/0101515 | A1* | 4/2016 | Lim | A61H 3/00 |
| | | | | 623/24 |
| 2016/0107309 | A1* | 4/2016 | Walsh | B25J 9/0006 |
| | | | | 248/550 |
| 2016/0143800 | A1* | 5/2016 | Hyung | A61H 3/00 |
| | | | | 623/32 |

FOREIGN PATENT DOCUMENTS

| | | |
|---|---|---|
| JP | 2014-018536 A | 2/2014 |
| JP | 2014073227 A | 4/2014 |
| JP | 2014184084 A | 10/2014 |
| JP | 2014195506 A | 10/2014 |
| KR | 20080075251 A | 8/2008 |
| KR | 20150039386 A | 4/2015 |

OTHER PUBLICATIONS

Wang, Shiqian et al., "Design and Control of the *Mindwalker* Exoskeleton", IEEE Transactions on Neural Systems and Rehabilitation Engineering, IEEE Service Center, New York, NY, vol. 23, No. 2, Mar. 1, 2015, pp. 277-286, XP011574792.

Tagliamonte, Nevio Luigi et al., "Human-Robot Interaction Tests on a Novel Robot for Gait Assistance", 2013 IEEE 13th International Conference on Rehabilitation Robotics (ICORR), IEEE, Jun. 24, 2013, pp. 1-6, XP032518116.

Extended European Search Report dated Jan. 31, 2017 for corresponding EP Patent Application No. 16163526.3.

* cited by examiner

METHOD AND APPARATUS FOR CALCULATING TORQUE OF WALKING ASSISTANCE DEVICE

CROSS-REFERENCE TO RELATED APPLICATION

This application is a continuation application of U.S. application Ser. No. 15/000,638, filed on Jan. 19, 2016, which claims priority under 35 U.S.C. § 119 to Korean Patent Application No. 10-2015-0113226, filed on Aug. 11, 2015, in the Korean Intellectual Property Office, the entire contents of each of which are incorporated herein by reference in its entirety.

BACKGROUND

1. Field

At least one example embodiment relates to a torque calculating method. For example, to a method of calculating a torque of a walking assistance device.

2. Description of the Related Art

With the onset of rapidly aging societies, a number of people may experience inconvenience and/or pain from joint problems. Thus, there is a growing interest in walking assistance devices enabling the elderly and/or patients having joint problems to walk with less effort. Furthermore, walking assistance devices increasing muscular strength of human bodies may be desired for military purposes.

In general, walking assistance devices may include body frames disposed on trunks of users, pelvic frames coupled to lower sides of the body frames to cover pelvises of the users, femoral frames disposed on thighs of the users, sural frames disposed on calves of the users, and/or pedal frames disposed on feet of the users. The pelvic frames and femoral frames may be connected rotatably by hip joint portions, the femoral frames and sural frames may be connected rotatably by knee joint portions, and/or the sural frames and pedal frames may be connected rotatably by ankle joint portions.

SUMMARY

Some example embodiments relate to a method of calculating an output torque of a walking assistance device.

In some example embodiments, the method may include determining a gait cycle based on a joint angle; determining a gait parameter with respect to a transition among predefined gait states based on the joint angle; and calculating the output torque based on the gait cycle and the gait parameter.

In some example embodiments, the determining the gait cycle comprises: calculating a gait frequency based on the joint angle; and determining the gait cycle based on the gait frequency.

In some example embodiments, the determining the gait parameter comprises: determining a current one of the gait states based on a previous one of the gait states and the joint angle; determining if the transition among the gait states occurred based on the previous one of the gait states and the current one of the gait states; and determining the gait parameter in response to a determination that the transition occurred.

In some example embodiments, the determining the gait parameter further includes determining a second gait cycle as the gait parameter, and the calculating the output torque includes calculating the output torque based on the gait cycle and the second gait cycle.

In some example embodiments, the determining the second gait cycle comprises: defining a value preset with respect to the current one of the gait states as a value of the second gait cycle.

In some example embodiments, the determining the gait parameter includes calculating a second gait frequency as the gait parameter, and the calculating the output torque includes calculating the output torque based on the gait cycle and the second gait frequency.

In some example embodiments, the calculating of the second gait frequency comprises: calculating the second gait frequency based on a period of the transition.

In some example embodiments, the determining the current one of the gait states comprises: determining a gait state corresponding to the joint angle, among the gait states with respect to the joint angle, to be the current one of the gait states.

In some example embodiments, the calculating the output torque comprises: determining whether a difference between the gait cycle and the gait parameter is greater than or equal to a threshold; and calculating the output torque based on the gait parameter in response to a determination that the difference is greater than or equal to the threshold.

In some example embodiments, the calculating the output torque comprises: determining whether a difference between the gait cycle and the gait parameter is greater than or equal to a threshold; and calculating the output torque based on the gait cycle and the gait parameter, if the difference is less than the threshold.

In some example embodiments, the calculating the output torque comprises: determining whether a condition is satisfied; and calculating the output torque based on the gait parameter, if the condition is satisfied.

In some example embodiments, the condition is an initial-stage-of-walking-condition.

In some example embodiments, the initial-stage-of-walking-condition is satisfied when the current gait state has been determined to be one of the gait states for less than a set number of times.

In some example embodiments, the calculating the output torque comprises: determining a final gait cycle based on the gait cycle and the gait parameter; and calculating the output torque corresponding to the final gait cycle.

In some example embodiments, the joint angle is an angle of at least one of a hip joint, a knee joint, and an ankle joint.

In some example embodiments, the determining the gait cycle comprises: determining the gait cycle using a particularly shaped adaptive oscillator (PSAO).

In some example embodiments, the determining the gait parameter comprises: determining the gait parameter based on a finite state machine (FSM).

Some example embodiments relate to a torque calculating apparatus.

In some example embodiments, the apparatus includes a receiver configured to receive a measurement of a joint angle; and a processor configured to, determine a gait parameter with respect to a transition among predefined gait states based on the joint angle, determine a gait cycle based on the joint angle, and determine an output torque based on the gait cycle and the gait parameter.

Some example embodiments relate to a torque calculating method.

In some example embodiments, the method includes obtaining a first gait cycle based on a measured joint angle;

obtaining a second gait cycle with respect to a transition among predefined gait states based on the joint angle; calculating a final gait cycle based on the first gait cycle and the second gait cycle when the transition occurs; and calculating a torque corresponding to the final gait cycle.

Some example embodiments relate to a method of calculating a torque to apply to a walking assistance device.

In some example embodiments, the method includes determining a current gait state within a gait cycle of the user based on a joint angle associated with a joint of the user; and calculating the torque based on the current gait state.

In some example embodiments, the calculating the torque calculates the torque using a particularly shaped adaptive oscillator (PSAO) and a finite state machine (FSM).

In some example embodiments, the method further comprises: determining, using the PSAO, the current gait state based on a trajectory of the joint angle associated with the joint of the user.

In some example embodiments, the method further comprises: setting a phase of an oscillator of the PSAO as the current gait state, if the oscillator has a fundamental frequency corresponding to a gait frequency.

In some example embodiments, the method further comprises: setting a phase of the FSM as the current gait state by overriding the PSAO, if the gait cycle has completed less than a threshold number of times.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
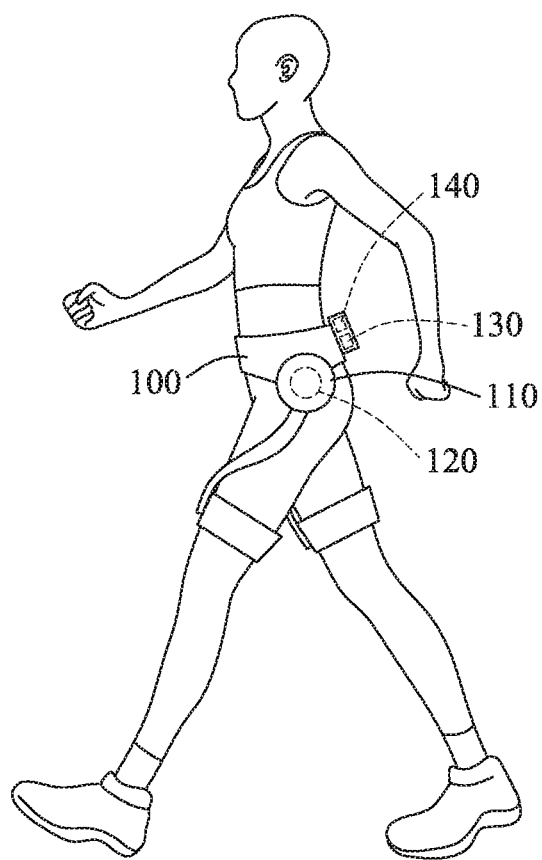
FIGS. 1 and 2 illustrate a walking assistance device according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

<Outline of Walking Assistance Device>

Figure 2:
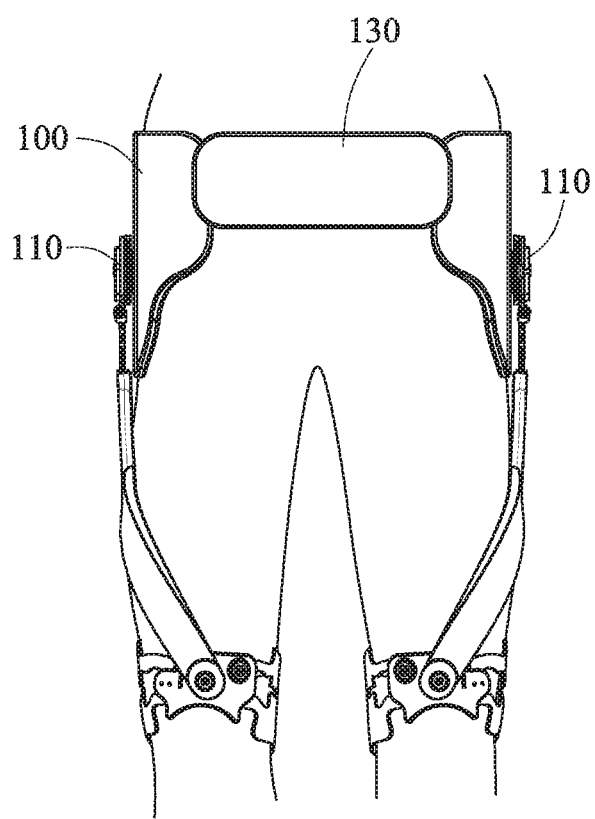

FIGS. 1 and 2 illustrate a walking assistance device according to at least one example embodiment.

Referring to FIG. 1, a walking assistance device 100 is attached to a user to assist the user, for example, with walking. The walking assistance device 100 may be a wearable device.

Although FIG. 1 illustrates a hip-type walking assistance device, the type of the walking assistance device is not limited thereto. The walking assistance device may be applicable to a walking assistance device that supports an entire pelvic limb, and a walking assistance device that supports a portion of a pelvic limb. The walking assistance device that supports a portion of a pelvic limb may be applicable to a walking assistance device that supports up to a knee, and a walking assistance device that supports up to an ankle.

Further, in other example embodiments, as discussed in detail with reference to FIGS. 20 through 22, a walking assistance device may support the whole body of the user.

Example embodiments described with reference to FIG. 1 and so on may be applicable to a hip-type walking assistance device, but are not limited thereto. The example embodiments may be applicable to all devices that assist walking of a user. For example, the example embodiments may be applicable to a whole body-type walking assistance device described with reference to FIGS. 20 through 22.

The walking assistance device 100 includes a driving portion 110, a sensor portion 120, an inertial measurement unit (IMU) sensor 130, and a controller 140.

The driving portion 110 may drive a hip joint of a user. For example, the driving portion 110 may be disposed on a right hip portion and/or a left hip portion of the user.

The driving portion 110 may include a motor configured to generate a rotational torque. For example, the driving portion 110 may include two motors each disposed on a respective one of the hip portions of the user.

The sensor portion 120 may measure an angle of the hip joint of the user while the user is walking. Information on the angle of the hip joint sensed by the sensor portion 120 may include an angle of a right hip joint, an angle of a left hip joint, a difference between the angle of the right hip joint and the angle of the left hip joint, and/or motion directions of both hip joints. For example, the sensor portion 120 may be disposed in the driving portion 110.

The sensor portion 120 may include a potentiometer. The potentiometer may sense an R-axis joint angle, an L-axis joint angle, an R-axis joint angular velocity, and/or an L-axis joint angular velocity with respect to a gait motion of the user.

The IMU sensor 130 may measure acceleration information and pose information while the user is walking. For example, the IMU sensor 130 may sense an X-axis acceleration, a Y-axis acceleration, a Z-axis acceleration, an X-axis angular velocity, a Y-axis angular velocity, and a Z-axis angular velocity with respect to the gait motion of the user.

The walking assistance device 100 may detect a point at which a foot of the user lands based on the acceleration information measured by the IMU sensor 130.

A pressure sensor (not shown) may be disposed on a sole of the user to detect the landing point of the foot of the user.

In addition to the sensor portion 120 and the IMU sensor 130, the walking assistance device 100 may include another sensor, for example, an electromyogram (EMG) sensor, configured to sense a change in a biosignal or a momentum of the user with respect to the gait motion.

The controller 140 may control the driving portion 110 to output a torque, an assistance force, and/or an assistance torque to assist walking of the user. For example, in the hip-type walking assistance device 100, two driving portions 110, in detail, a left hip driving portion and a right hip driving portion, may be provided. The controller 140 may output a control signal to control the driving portions 110 to generate torques. In some example embodiments, the controller 140 may output different control signals to each of the driving portions 110.

The driving portion 110 may generate a torque based on the control signal output from the controller 140.

The torque may be set by an external device, or may be set by the controller 140.

The walking assistance device 100 may include a right leg driving portion 110 and a left leg driving portion 110.

In an example, the controller 140 may be designed to control one of the driving portions 110. When the controller 140 controls one of the driving portions 110, a plurality of controllers 140 may be provided such that each of the controllers 140 controls a respective one of the driving portions 110.

In another example, the controller 140 may be designed to control both of the driving portions 110.

Figure 3:
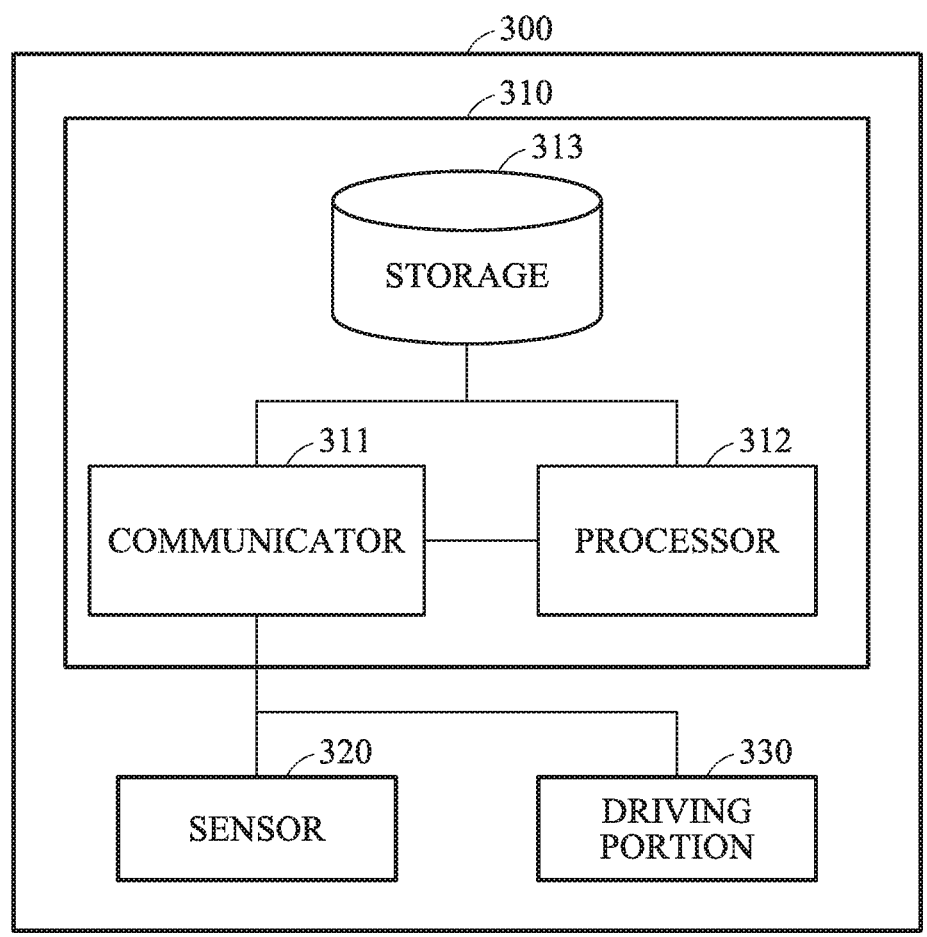
FIG. 3 is a block diagram illustrating a walking assistance device according to at least one example embodiment.

FIG. 3 is a block diagram illustrating a walking assistance device according to at least one example embodiment.

Referring to FIG. 3, a walking assistance device 300 includes a controller 310, a sensor 320, and a driving portion 330.

The walking assistance device 300 may correspond to the walking assistance device 100. For example, in some example embodiments, the controller 310 corresponds to the controller 140, the sensor 320 corresponds to the sensor portion 120, and the driving portion 330 corresponds to the driving portion 110.

The controller 310 includes a communicator 311, a processor 312, and a storage 313. The controller 310 may be referred to as a torque calculating apparatus.

The communicator 311 may exchange data with the sensor 320, and communicate with other devices. The communicator 311 may include transmitters and/or receivers. The transmitters may include hardware and any necessary software for transmitting signals including, for example, data signals and/or control signals. The receivers may include hardware and any necessary software for receiving signals including, for example, data signals and/or control signals.

The processor 312 may process data received by the communicator 311 and data stored in the storage 313. The processor 312 may be implemented by at least one semiconductor chip disposed on a printed circuit board. The processor 312 may be an arithmetic logic unit, a digital signal processor, a microcomputer, a field programmable array, a programmable logic unit, a microprocessor or any other device capable of responding to and executing instructions in a defined manner such that the processor 312 is programmed with instructions that configure the processor 313 into a special purpose computer to perform the operations illustrated in FIG. 5 to calculate an assistance torque utilizing both a particularly shaped adaptive oscillator (PSAO) and a Finite State Machine (FSM). Therefore the processor 312 may improve the functioning of the controller 140 itself by reducing (or, alternatively to minimize) an error in a measured joint angle using the PSAO, and reducing an amount of time used to obtain a gait frequency when the gait state changes quickly.

The storage 313 may store the data received by the communicator 311 and the data processed by the processor 312. The storage 313 may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The controller 310, the sensor 320, and the driving portion 330 will be described in detail with reference to FIGS. 4 through 19.

<Method of Calculating Assistance Torque of Walking Assistance Device>

Figure 4:
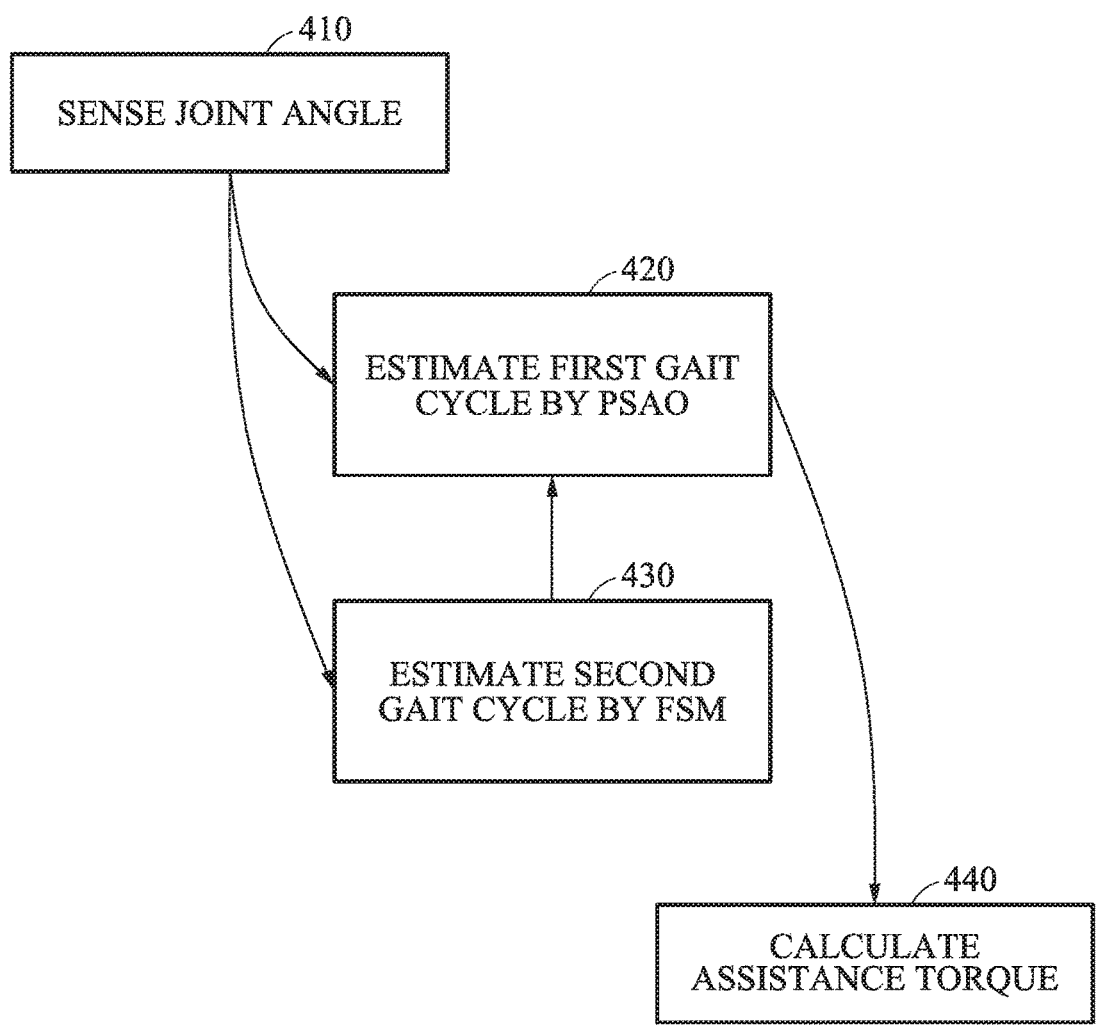
FIG. 4 is a flow illustrating a method of calculating an assistance torque according to at least one example embodiment.

FIG. 4 is a flowchart illustrating a method of calculating an assistance torque according to at least one example embodiment.

The walking assistance device 300 of FIG. 3 may provide (or, alternatively, continuously provide) a user with an assistance torque corresponding to a gait state while the user is walking.

The walking assistance device 300 may calculate the assistance torque based on a joint angle of the user. A joint may include a hip joint, a knee joint, and/or an ankle joint.

Referring to FIG. 4, in operation 410, the walking assistance device 300 may measure or sense a joint angle of a user. For example, a joint angle sensor of the walking assistance device 300 may measure the joint angle. The sensor 320 of FIG. 3 may include the joint angle sensor. In some example embodiments, the joint angle sensor may be attached around a joint of the user. In another example, the joint angle sensor may measure the joint angle by measuring angles of two supports that support a vicinity of the joint.

In operation 420, the walking assistance device 300 may estimate a first gait cycle by a particularly shaped adaptive oscillator (PSAO).

In operation 430, the walking assistance device 300 may estimate a second gait cycle by a finite state machine (FSM).

In some example embodiments, the walking assistance device 300 may estimate a final gait cycle based on the first gait cycle and the second gait cycle in operation 420.

In other example embodiments, in operation 420, the walking assistance device 300 may estimate the first gait cycle based on the second gait cycle such that the walking assistance device 300 calculates the second gait cycle in operation 430 prior to performing operation 420. Therefore, the first gait cycle may be the final gait cycle.

In operation 440, the walking assistance device 300 may calculate an assistance torque with respect to the final gait cycle.

The calculated assistance torque may be transferred to the driving portion 330. The driving portion 330 may generate the assistance torque by rotating a motor.

A method of calculating or obtaining an output torque using a particularly shaped adaptive oscillator (PSAO) and a finite state machine (FSM) will be described in detail with reference to FIGS. 5 through 19.

<Method of Calculating Output Torque Using PSAO and/or FSM>

Figure 5:
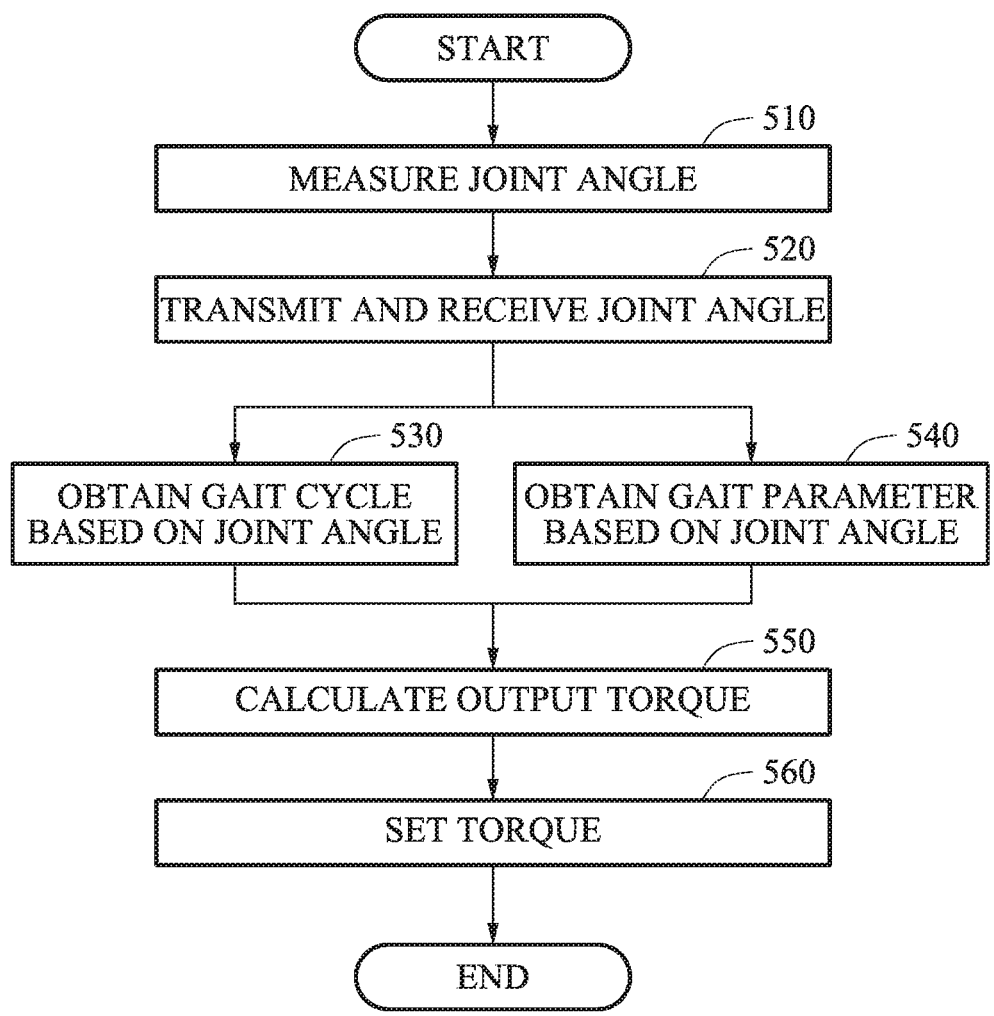
FIG. 5 is a flowchart illustrating a method of calculating an output torque according to at least one example embodiment.

FIG. 5 is a flowchart illustrating a method of calculating an output torque according to at least one example embodiment.

Referring to FIG. 5, in operation 510, the sensor 320 of FIG. 3 may measure a joint angle. For example, the sensor 320 may measure an angle of a hip joint of the user. The sensor 320 may measure the joint angle based on a desired (or, alternatively, a predetermined) period.

In operation 520, the communicator 311 receives the measured joint angle from the sensor 320, which transmits same. The sensor 320 and the communicator 311 may exchange data using a wireless local area network.

Since the joint angle is measured based on the desired (or, alternatively, the predetermined) period, the measured joint angles may create a trajectory corresponding to a time axis.

In operation 530, the processor 312 of FIG. 3 determines a gait cycle based on the joint angle. For example, the processor 312 may determine the gait cycle based on the trajectory with respect to the joint angle.

The processor 312 may continuously determine the gait cycle using a particularly shaped adaptive oscillator (PSAO). For example, the processor 312 may determine a current gait cycle based on a trajectory of a preset joint angle. The trajectory of the preset joint angle will be described in detail with reference to FIG. 8.

The gait cycle obtained using the PSAO may be a first gait cycle.

In some example embodiments, the controller 310 may include a single processor 312 such that operations 530 and 540 may be performed by the same processor 312.

In other example embodiments, the controller 310 of FIG. 3 may include a plurality of processors such that operations 530 and 540 may be performed by different ones of the plurality of processors 312.

Although operations 530 and 540 are performed by the same processor in the following descriptions, operations 530 and 540 may be performed by separate processors.

In operation 540, the processor 312 may obtain a gait parameter using a finite state machine (FSM). For example, the processor 312 may obtain the gait parameter with respect to a transition among a desired (or, alternatively, a predetermined) number of gait states included in the FSM based on the joint angle. The transition among the number of gait states will be described in detail with reference to FIGS. 12 through 14.

The gait parameter may include a second gait frequency and a second gait cycle measured using the FSM. The second gait frequency and the second gait cycle measured using the FSM will be described in detail with reference to FIG. 15.

In some example embodiments, the processor 312 may perform operations 530 and 540 in parallel such that the processor 312 determines gait cycle based on the PSAO and the gait parameter based on the FSM in parallel.

In other example embodiments, the processor 312 may determine the gait parameter in operation 540, and, in operation 530 may use the gait parameter as a reference value to determine the gait cycle by the PSAO.

In operation 550, the processor 312 may calculate or obtain an output torque based on the gait cycle and the gait parameter.

For example, in some example embodiments, the processor 312 may determine a final gait cycle based on the first gait cycle and the gait parameter, for example, the second gait cycle. The processor 312 may calculate an output torque corresponding to the final gait cycle.

In other example embodiments, when the gait parameter is used as the reference value to determine the gait cycle by the PSAO, the processor 312 may calculate an output torque corresponding to the first gait cycle.

A method of calculating an output torque will be described in detail with reference to FIGS. 16 through 18.

In operation 560, the processor 312 may set a signal with respect to the calculated output torque in the driving portion 330 of FIG. 3. For example, the processor 312 may set the output torque in the driving portion 330 by transferring the signal with respect to the output torque to the driving portion 330 through the communicator 311.

The driving portion 330 may generate a torque using a motor based on the signal.

Figure 6:
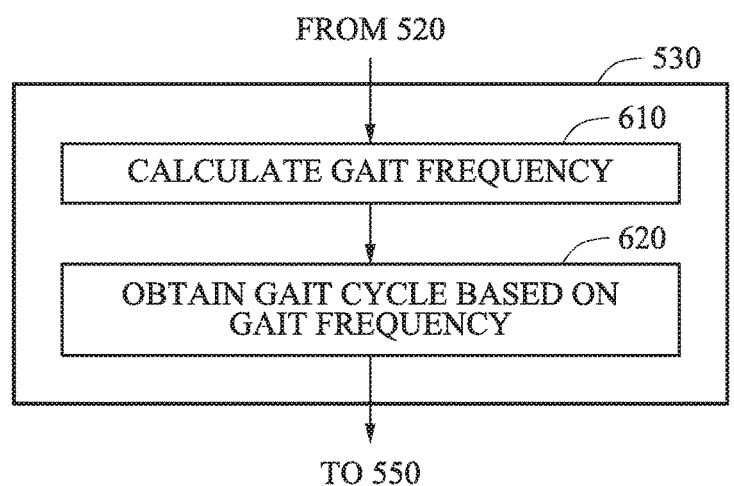
FIG. 6 is a flowchart illustrating a method of obtaining a gait cycle according to at least one example embodiment.

FIG. 6 is a flowchart illustrating a method of obtaining a gait cycle according to at least one example embodiment.

A particularly shaped adaptive oscillator (PSAO) may be a signal processing module that receives a measured joint angle as an input and outputs a gait cycle.

The processor 312 of FIG. 3 may include software that, when executed, configures the processor 312 as a PSAO module. In the following descriptions, descriptions of the PSAO may be construed as descriptions of the processor 312.

Operation 530 of FIG. 5 may include operations 610 and 620.

Figure 7:
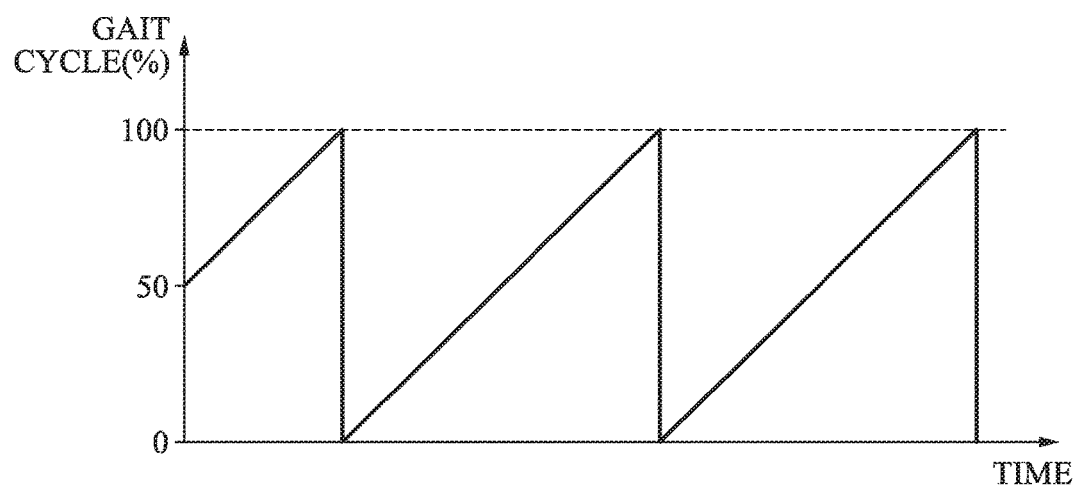
FIG. 7 illustrates a gait cycle obtained by a particularly shaped adaptive oscillator (PSAO) according to at least one example embodiment.
Figure 8:
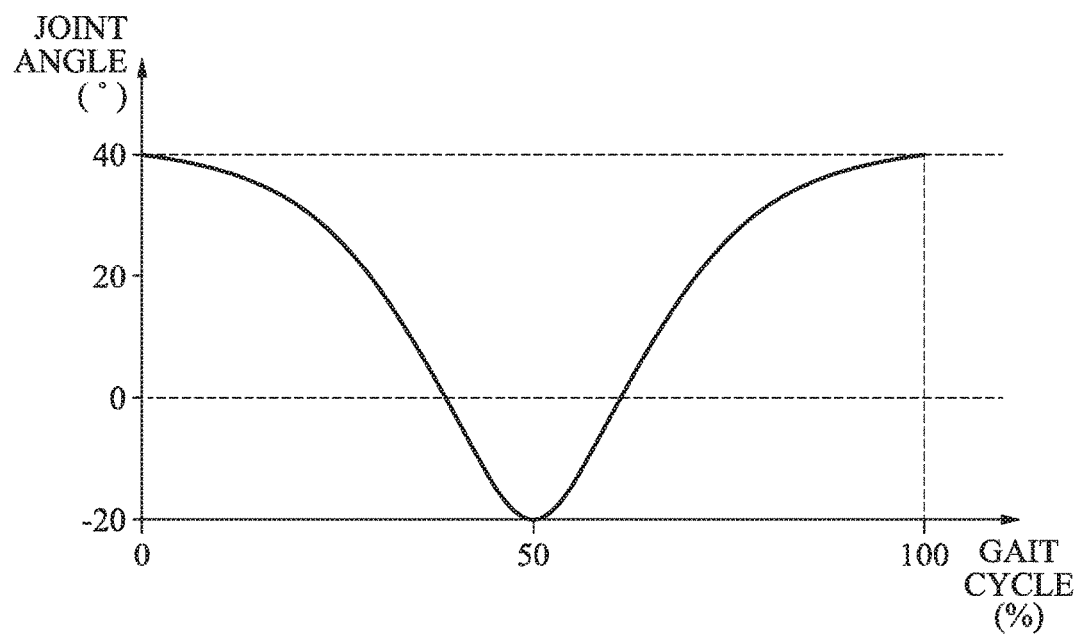
FIG. 8 illustrates a reference trajectory of a joint angle of a hip joint with respect to a gait cycle according to at least one example embodiment.

Referring to FIGS. 6 to 8, in operation 610, the processor 312 may calculate a gait frequency.

As shown in FIG. 8, a reference trajectory of a joint angle stored in the PSAO, hereinafter, simply referred to as the reference trajectory, may be a reference trajectory of a joint angle with respect to a gait cycle.

The gait cycle may be a single period from an instant at which a first leg touches the ground to an instant at which the first leg touches the ground again.

As shown in FIG. 7, the gait cycle may be defined as a variable that increases linearly during a single period. Although FIG. 7 illustrates a trajectory of only one of both legs, the same descriptions may be applicable to a trajectory of the other leg.

For example, in the gait cycle, 0% may indicate a state in which the leg touches the ground after performing a swing, a range between 0% and 60% may indicate a state in which the leg is in a stance that supports a body, a range between 60% and 100% may indicate a state in which the leg is performing a swing, and 100% may indicate a state immediately before the leg touches the ground after performing a swing.

The PSAO may include a plurality of oscillators, each having an offset, a fundamental frequency, or a frequency modulated from the fundamental frequency. The plurality of oscillators may have respective phases and amplitudes. The frequency modulated from the fundamental frequency may be an integer multiple frequency of the fundamental frequency.

In detail, the PSAO may obtain angles of the plurality of oscillators by applying a reference trajectory, the phases, and the amplitudes to the plurality of oscillators, each having the fundamental frequency and a frequency corresponding to an integer multiple of the fundamental frequency.

The PSAO may generate an overlapping angle by overlapping the angles obtained from the plurality of oscillators. The PSAO may generate an overlapping angle trajectory by combining generated overlapping angles in an order of a gait cycle. The PSAO may iteratively correct the fundamental frequency, the offset, the phase, and the amplitude of each of the plurality of oscillators to reduce (or, alternatively to minimize) an error between the overlapping angle and the measured joint angle.

By iteratively performing the correction, the overlapping angle trajectory may be approximated to a trajectory of the measured joint angle. The fundamental frequency, the offset, and the amplitude of each of the plurality of oscillators may converge to a desired (or, alternatively, a predetermined) value to correspond to the trajectory of the measured joint angle.

When the generated overlapping angle trajectory corresponds to the trajectory of the measured joint angle, the fundamental frequency of the PSAO may correspond to the gait frequency. A phase of an oscillator having the fundamental frequency may correspond to a current gait phase.

Hereinafter, a method of correcting a fundamental frequency, an offset, a phase, and an amplitude of each of a plurality of oscillators for the aforementioned PSAO to periodically correspond to a trajectory of a measured joint angle, and a method of calculating a gait phase will be described using equations.

$$\theta_p(n) = \alpha_0 + \sum_{i=1} \alpha_i(n) f(\varphi_i(n)) \qquad \text{[Equation 1]}$$

The processor 312 may use Equation 1 to calculate an overlapping angle.

In Equation 1, i denotes a plurality of oscillators of a PSAO, n denotes an index of a measurement and correction cycle of a joint angle, $\theta_p$ denotes an overlapping angle, $\alpha_o$ denotes an offset of the overlapping angle, $\alpha_i$ denotes an amplitude of an i-th oscillator, $f(\varphi)$ denotes a function of a reference trajectory, and $\varphi_i$ denotes a phase of the i-th oscillator.

$$\varepsilon(n) = \theta_h(n) - \theta_p(n) \qquad \text{[Equation 2]}$$

The processor 312 may use Equation 2 to calculate an error value. The error value may be a difference value between a measured joint angle and the overlapping angle calculated using Equation 1.

In Equation 2, ε denotes an error value, and $\theta_h$ denotes a measured joint angle.

$$f'(\varphi) = \frac{\partial f}{\partial \varphi}(\varphi) \qquad [\text{Equation 3}]$$

The processor 312 may use Equation 3 to expresses a variation in a joint angle reference trajectory of an oscillator of a PSAO.

$$\alpha_1(n+1) = \max\left\{0, \alpha_i(n) + T_s \frac{k_\alpha}{i} \varepsilon f(\varphi_i(n))\right\} \qquad [\text{Equation 4}]$$

The processor 312 may use Equation 4 to correct an amplitude of an oscillator having an i-fold frequency of a fundamental frequency, among a plurality of oscillators of a PSAO.

In Equation 4, an amplitude correction quantity of an oscillator may be calculated by multiplying an amplitude correction gain, an error value, and a resulting value obtained by applying a phase of an i-th oscillator to a function of a reference trajectory, and dividing a resulting value of the multiplying by an index of the oscillator.

In Equation 4, a current amplitude correction value may be calculated by multiplying the amplitude correction quantity by a correction iteration period $T_s$, and adding a previous amplitude correction value to a resulting value of the multiplying.

In Equation 4, the current amplitude correction value may be restricted not to be less than "0". An error value between the measured joint angle and the overlapping angle may be reduced through Equation 4.

In Equation 4, $k_\alpha$ denotes an amplitude correction gain, $T_s$ denotes a measurement and correction iteration period of a joint angle. The sampling period may be within a range of about 1 to 10 milliseconds (ms).

$$\varphi_i(n+1) = \varphi_i(n) + T_s\left(i\omega(n) + k_\varphi \frac{\varepsilon}{\sum \alpha_i(n)} f'(\varphi_i(n))\right) \qquad [\text{Equation 5}]$$

The processor 312 may use Equation 5 to calculate a phase of an oscillator having an i-fold frequency of a fundamental frequency, among a plurality of oscillators of a PSAO.

The i-th oscillator may have the i-fold frequency of the fundamental frequency. A phase increment may change due to a value obtained by multiplying an error value by a variation in a reference trajectory. Thus, an error value between a trajectory of a measured joint angle and an overlapping angle trajectory may decrease.

To correct a phase, a first value may be calculated by multiplying an index of an oscillator by a fundamental frequency of the PSAO, and a second value may be calculated by multiplying a phase correction gain, an error, and a resulting value obtained by applying a phase of the oscillator to a function with respect to a variation in a reference trajectory, and dividing a resulting value of the multiplying by a sum of amplitudes of the plurality of oscillators. A phase correction value of the i-th oscillator may be calculated by adding the first value and the second value. By multiplying a correction cycle period by the calculated correction value, and adding a phase corrected at a previous sampling time to a resulting value of the multiplying, a currently corrected phase of the i-th oscillator may be calculated.

In Equation 5, $k_\varphi$ denotes a phase correction gain, and ω denotes a fundamental frequency of a PSAO.

$$\omega(n+1) = \omega(n) + T_s\left(k_\omega \frac{\varepsilon}{\sum \alpha_i} f'(\varphi_1) + \sum k_\varphi e^{\frac{(\omega_{ext}-\omega)^2}{2}}(\omega_{ext}-\omega)\right) \qquad [\text{Equation 6}]$$

The processor 312 may use Equation 6 to correct a fundamental frequency of a PSAO.

In Equation 6, a third value may be calculated by multiplying a frequency correction gain, an error value, and a resulting value obtained by applying a phase of a first oscillator to a function with respect to a variation in a reference trajectory, and dividing a resulting value of the multiplying by a sum of amplitudes of a plurality of oscillators.

In Equation 6, a fourth value may be obtained by adding, with respect to all joints excluding the joint calculated in Equation 6, values obtained by multiplying a coupling frequency gain, a natural exponential value of a value obtained by multiplying −½ by a square of a difference between a frequency of a joint angle trajectory measured by another PSAO in another aspect and a fundamental frequency of the present PSAO, and a difference between the frequency of the joint angle trajectory measured in the other aspect and the fundamental frequency.

For example, the present PSAO may measure a frequency of an angle trajectory of a right hip joint, and the other PSAO may measure a frequency of an angle trajectory of a left hip joint.

The third value of Equation 6 may be a value to correct the fundamental frequency so that the fundamental frequency of the PSAO may correspond to a frequency of the trajectory of the measured joint angle.

In general, an estimated frequency of a left joint angle trajectory may coincide with an estimated frequency of a right joint angle trajectory. However, when the estimated frequencies do not coincide, the fourth value may be a value to correct the fundamental frequency to match the different frequencies.

In detail, a natural exponential portion of the fourth value may converge to "0" when the difference between the two frequencies is great. Thus, coupling between the two frequencies may be blocked. The natural exponential portion of the fourth value may induce the two frequencies to be identical to each other when the difference between the two frequencies is modest.

A sum of the third value and the fourth value may be a correction quantity of the fundamental frequency of the PSAO. By multiplying the sum of the third value and the fourth value by the correction period, and adding a previous correction fundamental frequency to a resulting value of the multiplying, a current correction fundamental frequency may be calculated.

In Equation 6, $k_\omega$ denotes a frequency correction gain, $k_c$ denotes a coupling frequency gain, and $\omega_{ext}$ denotes a frequency of a joint angle trajectory measured by another PSAO in another aspect.

$$\alpha_o(n+1) = \alpha_o(n) + T_s k_o \varepsilon \qquad [\text{Equation 7}]$$

The processor 312 may use Equation 7 to correct an offset of an overlapping angle of a PSAO.

Equation 7 may reduce a calculation error resulting from an offset by correcting the offset of the overlapping angle of the PSAO to correspond to an offset of a measured joint angle.

In Equation 7, $k_o$ denotes an offset correction gain. Through the aforementioned equations, the PSAO may match the overlapping angle trajectory and the trajectory of the measured joint angle by continuously calculating, during a gait duration, an overlapping angle to correspond to the measured joint angle.

The processor 312 may include a PSAO or a PSAO module. For example, the processor 312 may include a PSAO for a left hip joint and a PSAO for a right hip joint.

The processor 312 may use Equations 1 through 7 to calculate the gait frequency.

In operation 620, the processor 312 may obtain a gait cycle based on the gait frequency.

The processor 312 may obtain the gait cycle using a phase compensated adaptive oscillator (PCAO).

In an example, the PCAO may be a signal processing module that receives a measured joint angle as an input, and outputs a current gait cycle.

In another example, the PCAO may be a subordinate concept of a PSAO, and may substitute a reference trajectory of the PSAO with a sinusoidal wave.

The processor 312 may include software that, when executed by the processor 312, configures the processor 212 as a PCAO module. In the following descriptions, descriptions of the PCAO may construed as descriptions of the processor 312.

The PCAO may include a first adaptive oscillator AO-1, a second adaptive oscillator AO-2, and a gait cycle calculator.

The first adaptive oscillator AO-1 may receive a measured joint angle as an input, and calculate a first overlapping angle trajectory by overlapping trigonometrical functions having a fundamental frequency and a frequency modulated from the fundamental frequency. The first adaptive oscillator AO-1 may calculate a first phase corresponding to a phase of a trigonometrical function having the fundamental frequency.

The second adaptive oscillator AO-2 may apply a reference angle on a reference trajectory corresponding to a current gait cycle to the trigonometrical functions having the fundamental frequency and the frequency modulated from the fundamental frequency based on the current gait cycle calculated by the gait cycle calculator. The second adaptive oscillator AO-2 may calculate a second overlapping angle trajectory by overlapping the trigonometrical functions to which the reference angle is applied. The second adaptive oscillator AO-2 may calculate a second phase corresponding to a phase of a trigonometrical function having the fundamental frequency.

The first adaptive oscillator AO-1 of the PCAO is a module that calculates only a phase corresponding to an angle of a currently measured joint. Thus, the first adaptive oscillator AO-1 may not compensate for the first overlapping angle trajectory with the second overlapping angle trajectory calculated based on the reference trajectory while the user is walking.

To compensate for the first overlapping angle trajectory with the second overlapping angle trajectory, the second adaptive oscillator AO-2 of the PCAO may be additionally included.

The gait phase calculator may calculate a current gait phase by reflecting a phase difference between the first phase and the second phase based on the first phase calculated by the first adaptive oscillator AO-1 and the second phase calculated by the second adaptive oscillator AO-2.

The first phase output from the first adaptive oscillator AO-1 may be a phase of the first overlapping angle trajectory overlapped by applying the measured joint angle to trigonometrical functions having a fundamental frequency of the first adaptive oscillator AO-1 and a frequency modulated from the fundamental frequency. The first phase may be a phase of a trigonometrical function having the fundamental frequency, among the trigonometrical functions constituting the phase of the first overlapping angle trajectory.

The gait cycle may use an instant at which a heel of a foot touches the ground as a reference point in time.

The first phase is not calculated under an assumption that the instant at which a heel of a foot touches the ground is the reference point in time. Thus, the first phase may not correspond to the gait cycle. To compensate for such a difference in the reference point in time, the gait phase calculator may determine the gait cycle by correcting the first phase.

The first phase may be corrected by calculating the second overlapping angle trajectory using the second adaptive oscillator AO-2, and comparing the second phase corresponding to the phase of the second overlapping angle trajectory to the first phase.

The second phase calculated by the second adaptive oscillator AO-2 based on the reference angle of the reference trajectory corresponding to the gait cycle may be a phase of the second overlapping angle trajectory calculated by overlapping trigonometrical functions having a fundamental frequency of the second adaptive oscillator AO-2 and a frequency modulated from the fundamental frequency. The second phase may be a phase of a trigonometrical function having the fundamental frequency, among the trigonometrical functions constituting the phase of the second overlapping angle trajectory.

The PCAO may calculate the gait cycle by compensating for the first phase based on a phase difference between the second phase and the first phase accumulated by the gait phase calculator.

The first adaptive oscillator AO-1 and the second adaptive oscillator AO-2 may be adaptive oscillator (AO) modules.

The processor 312 may perform the operations of the first adaptive oscillator AO-1 and the second adaptive oscillator AO-2 using the following equations.

$$\theta_p(n) = \alpha_0 + \sum_{i=1} \alpha_i(n)\sin(\varphi_i(n)) \quad \text{[Equation 8]}$$

The processor 312 may use Equation 8 to calculate overlapping angles in the first adaptive oscillator AO-1 and the second adaptive oscillator AO-2.

An overlapping angle may be calculated by adding an offset to a sum of values obtained by multiplying values obtained by applying phases of a plurality of oscillators constituting a single AO to a sine function by amplitudes of the respective oscillators.

The PSAO may calculate an overlapping angle to correspond to the measured joint angle, and continuously perform the calculation during a gait time, thereby approximating the overlapping angle to the trajectory of the measured joint angle.

In Equation 8, i denotes indices of a plurality of oscillators, n denotes an index of a measurement and correction cycle of a joint angle, $\theta_p$ denotes an overlapping angle, $\alpha_o$ denotes an offset of the overlapping angle, $\alpha_i$ denotes an amplitude of an i-th oscillator, and $\varphi_i$ denotes a phase of the i-th oscillator.

$$\varepsilon(n)=\theta_h(n)-\theta_p(n) \quad \text{[Equation 9]}$$

The processor 312 may use Equation 9 to calculate an error value in a single AO.

The error value may be a difference value between an input value of the AO and the overlapping angle calculated by Equation 8. An input value of the first adaptive oscillator AO-1 may be the measured joint angle, and an input value of the second adaptive oscillator AO-2 may be the reference angle corresponding to the current gait phase.

In Equation 9, $\varepsilon$ denotes an error value, and $\theta_h$ denotes an input value of an AO.

$$\alpha_i(n+1) = \max\left\{0, \alpha_i(n) + T_s \frac{k_a}{i}\varepsilon\sin(\varphi_i,(n))\right\} \quad \text{[Equation 10]}$$

The processor 312 may use Equation 10 to correct amplitudes of oscillators having an i-fold frequency of a fundamental frequency, among a plurality of oscillators of a PCAO.

An amplitude correction quantity of an oscillator may be calculated by dividing, by an oscillator index, a value obtained by multiplying an amplitude correction gain, an error value, and a resulting value obtained by applying a phase of an i-th oscillator to a sine function. A current amplitude correction value may be calculated by multiplying the amplitude correction quantity by a correction iteration period $T_s$, and adding a previous amplitude correction value to a resulting value of the multiplying.

The current amplitude correction value may be restricted not to be less than "0".

An error value between the measured joint angle and the overlapping angle may be reduced through Equation 10.

In Equation 10, $k_a$ denotes an amplitude correction gain, $T_s$ denotes a measurement and correction iteration period of a joint angle. The sampling period may be within a range of about 1 to 10 ms.

$$\varphi_i(n+1) = \varphi_i(n) + T_s\left(i\omega(n) + k_\varphi \frac{\varepsilon}{\sum \alpha_i(n)}\cos(\varphi_i(n))\right) \quad \text{[Equation 11]}$$

The processor 312 may use Equation 11 to calculate phases of oscillators having an i-fold frequency of a fundamental frequency, among a plurality of oscillators of a PCAO.

The i-th oscillator may have the i-fold frequency of the fundamental frequency.

A phase increment may change due to a value obtained by multiplying an error value by a cosine function value. Thus, an error value between an input of an AO and an overlapping angle of the AO may decrease.

To correct a phase, a fifth value may be calculated by multiplying an index of an oscillator by a fundamental frequency of the AO.

A sixth value may be calculated by multiplying a phase correction gain, an error, and a resulting value obtained by applying a phase of a corresponding oscillator to a cosine function, and dividing a resulting value of the multiplying by a sum of amplitudes of the plurality of oscillators.

A phase correction value of the i-th oscillator may be calculated by adding the fifth value and the sixth value. By multiplying the phase correction value by a period of a correction cycle, and adding a previous correction phase to a resulting value of the multiplying, a currently corrected phase of the i-th oscillator may be calculated.

In Equation 11, $k_\varphi$ denotes a phase correction gain, and $\omega$ denotes a fundamental frequency of an AO.

$$\omega(n+1) = \quad \text{[Equation 12]}$$
$$\omega(n) + T_s\left(k_\omega \frac{\varepsilon}{\sum \alpha_i}\cos(\varphi_1) + \sum k_\varphi e^{\frac{(\omega_{ext}-\omega)^2}{2}}(\omega_{ext}-\omega)\right)$$

The processor 312 may use Equation 12 to correct a fundamental frequency of a PCAO.

A seventh value may be calculated by multiplying a frequency correction gain, an error value, and a resulting value of applying a phase of a first oscillator to a function with respect to a variation in a reference trajectory.

An eighth value may be obtained by adding, with respect to all joints excluding the joint calculated in Equation 12, values of obtained by multiplying a coupling frequency gain, a natural exponential value of a value obtained by multiplying $-\frac{1}{2}$ by a square of a difference between a frequency of a joint angle trajectory measured by another PCAO in another aspect and a fundamental frequency of the AO of the present PCAO, and a difference between the frequency of the joint angle trajectory measured in the other aspect and the fundamental frequency.

For example, the present PCAO may measure a frequency of an angle trajectory of a right hip joint, and the other PCAO may measure a frequency of an angle trajectory of a left hip joint.

The seventh value of Equation 12 may be a value to correct the fundamental frequency so that the fundamental frequency of the AO may correspond to a frequency of the trajectory of the measured joint angle.

In general, an estimated frequency of a left joint angle trajectory may coincide with an estimated frequency of a right joint angle trajectory. When the estimated frequencies are different from each other, the eighth value may be a value to correct the fundamental frequency to match the different frequencies.

In detail, a natural exponential portion of the eighth value may converge to "0" when the difference between the two frequencies is great. Thus, coupling between the two frequencies may be blocked. The natural exponential portion of the eighth value may induce the two frequencies to be identical to each other when the difference between the two frequencies is modest.

A sum of the seventh value and the eighth value may be a correction quantity of the fundamental frequency of the AO. By multiplying the sum of the seventh value and the eighth value by a correction period, and adding a previous correction fundamental frequency to a resulting value of the multiplying, a current correction fundamental frequency may be calculated.

In Equation 12, $k_\omega$ denotes a frequency correction gain, $k_c$ denotes a coupling frequency gain, and $\omega_{ext}$ denotes a frequency of a joint angle trajectory measured by another PCAO in another aspect.

$$\alpha_o(n+1)=\alpha_o(n)+T_s k_o \varepsilon \quad \text{[Equation 13]}$$

Equation 13 is an equation to correct an offset of an overlapping angle of a PCAO.

Equation 13 may reduce a calculation error resulting from an offset by correcting the offset of the overlapping angle of the PCAO to correspond to an offset of a measured joint angle.

In Equation 13, $k_o$ denotes an offset correction gain.

$$\varphi_{GC}=\varphi_1+\int(\varphi_1-\varphi_2) \quad \text{[Equation 14]}$$

The processor 312 may use Equation 14 to calculate a current gait cycle based on a first phase and a second phase.

By adding, to the first phase, a value obtained by accumulating the phase difference between the first phase and the second phase at each cycle, the gait cycle may be calculated. As the cycle to compensate for the phase difference between the first phase and the second phase is repeated, the phase difference between the first phase and the second phase may converge to a desired (or, alternatively, a predetermined) value.

Using Equations 8 through 14, the processor 312 configured as the PCAO may obtain the gait cycle corresponding to the reference trajectory and the trajectory of the measured joint angle. The obtained gait cycle may be a first gait cycle.

The processor 312 may include a PCAO or PCAO module. For example, the processor 312 may include a PCAO for a left hip joint and a PCAO for a right hip joint.

FIG. 7 illustrates a gait cycle obtained by a PSAO according to at least one example embodiment.

The illustrated gait cycle shows an ideal gait cycle that may be obtained from a gait start time. The ideal gait cycle may have a value that increases linearly from a start of a gait.

FIG. 8 illustrates a reference trajectory of a joint angle of a hip joint with respect to a gait cycle according to at least one example embodiment.

In a period in which a joint angle of a hip joint has a positive value, a leg of a user is in front of a central axis of the user. In a period in which the joint angle of the hip joint has a negative value, the leg of the user is behind the central axis of the user.

In the example of FIG. 8, the reference trajectory is set to have a maximum joint angle of 40 degrees, and a minimum joint angle of −20 degrees.

Figure 9:
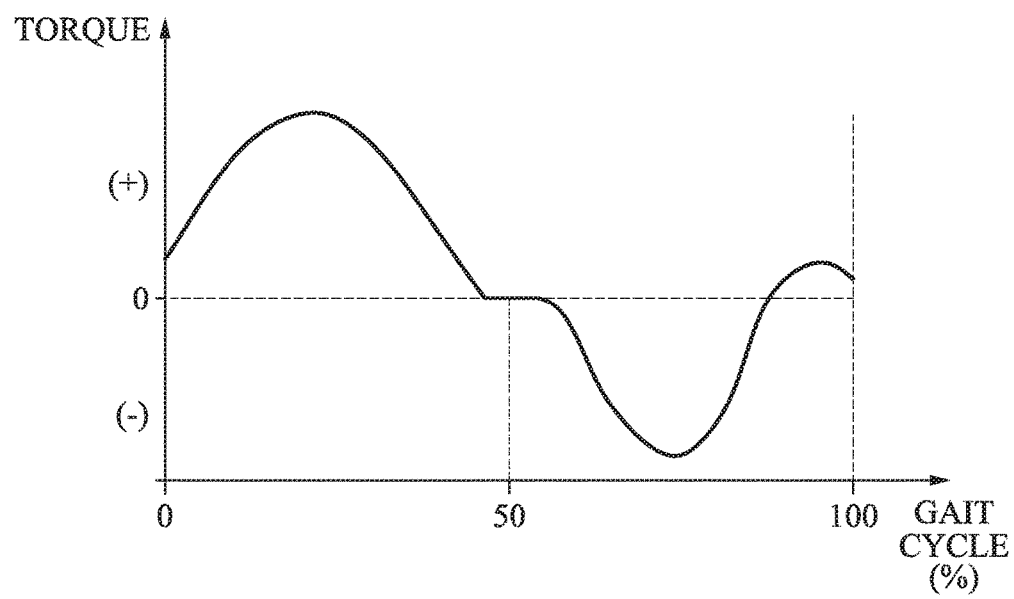
FIG. 9 illustrates an assistance torque set with respect to a gait cycle according to at least one example embodiment.

FIG. 9 illustrates an assistance torque set with respect to a gait cycle according to at least one example embodiment.

When a current gait cycle is determined, an assistance torque corresponding to the obtained gait cycle may be calculated. For example, when the current gait cycle corresponds to 60%, an assistance torque corresponding to the gait cycle 60% may be calculated.

An assistance torque having a positive value may provide a force in a direction in which a leg moves from front to back. Conversely, an assistance torque having a negative value may provide a force in a direction in which a leg moves from back to front.

A graph of FIG. 9 illustrates an assistance torque calculated with respect to a reference trajectory. The calculated assistance torque may change based on a trajectory of the obtained joint angle. For example, when the measured gait frequency is greater than a preset gait frequency, the assistance torque may increase.

A method of calculating an assistance torque or an output torque will be described in detail with reference to FIGS. 16 through 18.

Figure 10:
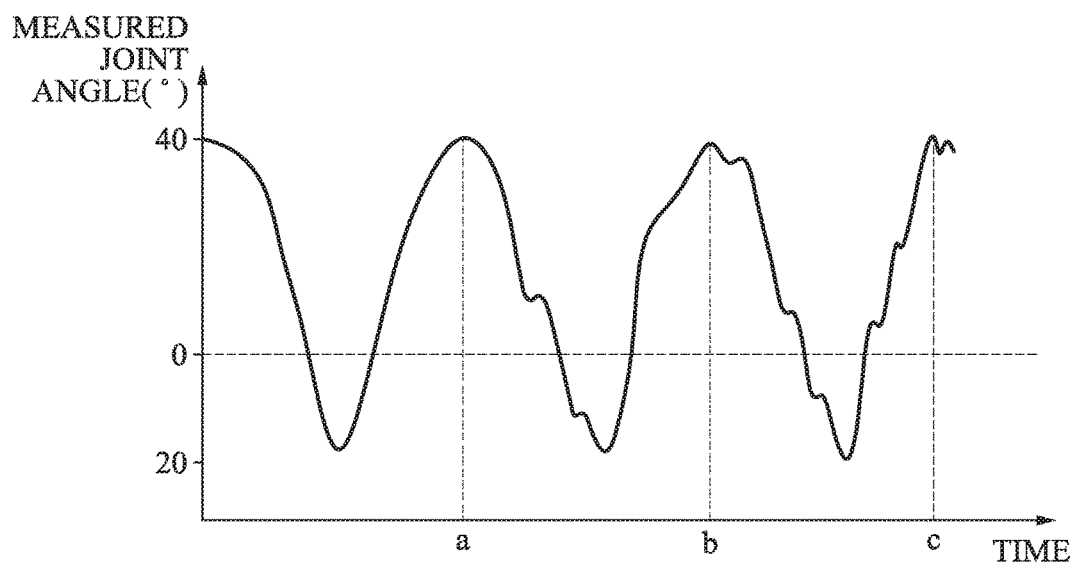
FIG. 10 illustrates a trajectory of a measured joint angle of a hip joint according to at least one example embodiment.

FIG. 10 illustrates a trajectory of a measured joint angle of a hip joint according to at least one example embodiment.

The processor 312 of FIG. 3 may generate a trajectory of a joint angle based on a measured joint angle.

The processor 312 may obtain a current gait cycle based on the trajectory of the measured joint angle and a reference trajectory. For example, the processor 312 may calculate a gait frequency indicated by the trajectory of the measured joint angle using a PSAO. The processor 312 may obtain the current gait cycle based on the gait frequency.

Figure 11:
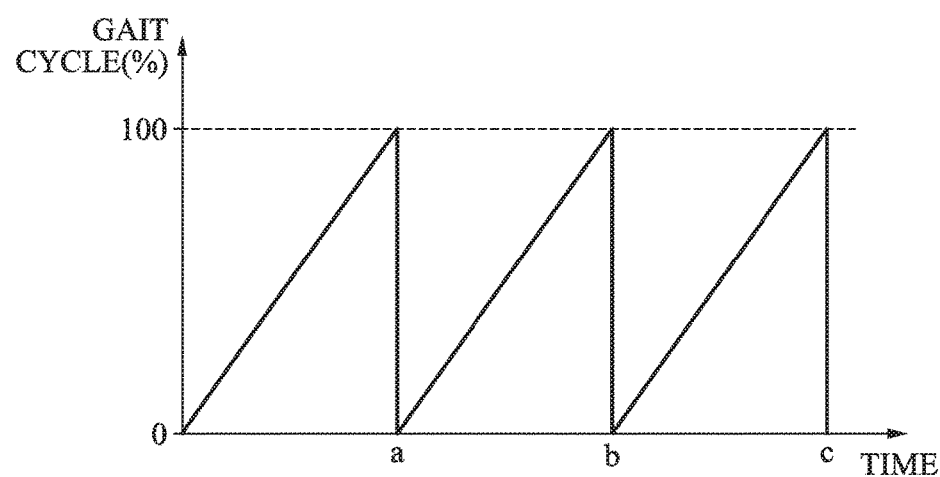
FIG. 11 illustrates a gait cycle with respect to a time according to at least one example embodiment.

FIG. 11 illustrates a gait cycle with respect to a time according to at least one example embodiment.

A gait cycle obtained using a PSAO after a desired (or, alternatively a predetermined) amount of time elapses from a gait start time may show a shape of a function that increases linearly. When a gait speed is relatively constant, the obtained gait cycle may be almost similar to a gait cycle of a true value.

A method of obtaining a gait cycle using a PSAO may not estimate a gait cycle of a true value quickly in a case in which a gait state changes rapidly. For example, the case in which the gait state changes rapidly may include a case in which a gait is started, and a case in which a gait speed is changed suddenly.

To prepare for such a situation, the processor 312 may employ a FSM in addition to the method using a PSAO.

A method additionally using an FSM will be described in detail with reference to FIGS. 12 through 15.

<Method Using PSAO and FSM>

Figure 12:
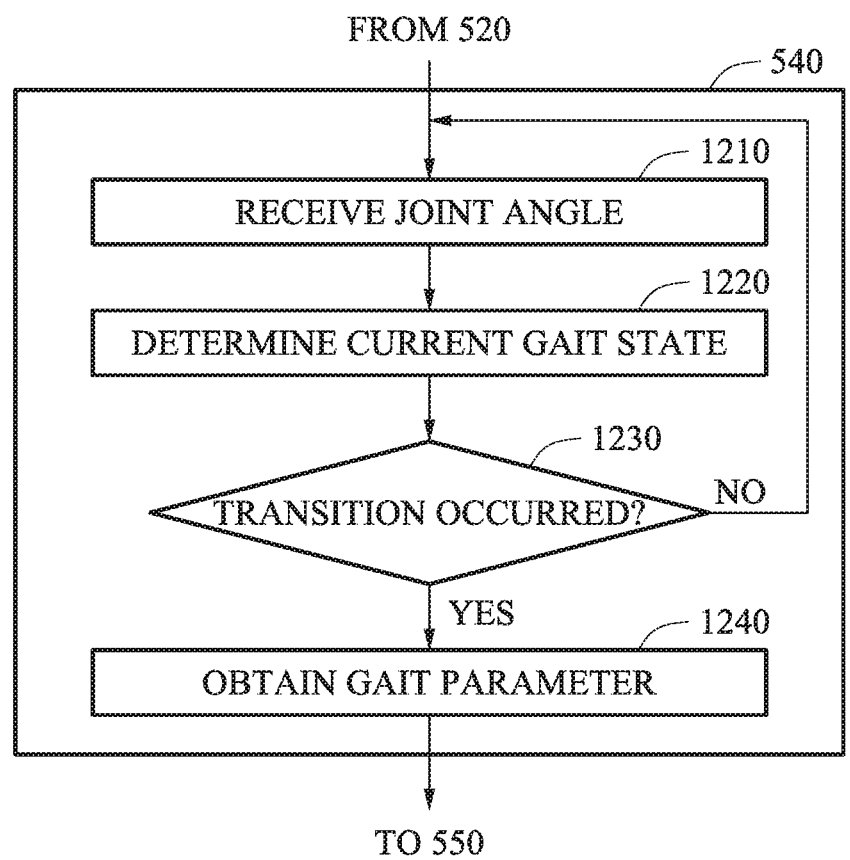
FIG. 12 is a flowchart illustrating a method of obtaining a gait parameter according to at least one example embodiment.

FIG. 12 is a flowchart illustrating a method of obtaining a gait parameter according to at least one example embodiment.

Referring to FIG. 12, operation 540 of FIG. 5 may include operations 1210 through 1240.

In operation 1210, the processor 312 of FIG. 3 may receive a measured joint angle. The joint angle may be a current joint angle.

In operation 1220, the processor 312 may determine a current gait state based on the joint angle.

In some example embodiments, the processor 312 may determine a gait state corresponding to the measured joint angle, among a desired (or, alternatively, a predetermined) number of gait states with respect to a joint angle, to be the current gait state.

In other example embodiments, the processor 312 may determine the current gait state based on a previous gait state and the joint angle.

When the same joint angle is measured, the current gait state may be determined to differ based on the previous gait state.

The gait states will be described in detail with reference to FIG. 13.

In operation 1230, the processor 312 may verify whether a transition among the gait states occurred by comparing the previous gait state to the current gait state.

In response to a verification that the transition did not occur, the processor 312 may re-perform operation 1210.

In operation 1240, the processor 312 may obtain a gait parameter in response to a verification that the transition occurred. For example, the gait parameter may include a second gait cycle and a second gait frequency.

The second gait cycle and the second gait frequency will be described in detail with reference to FIG. 15.

Figure 13:
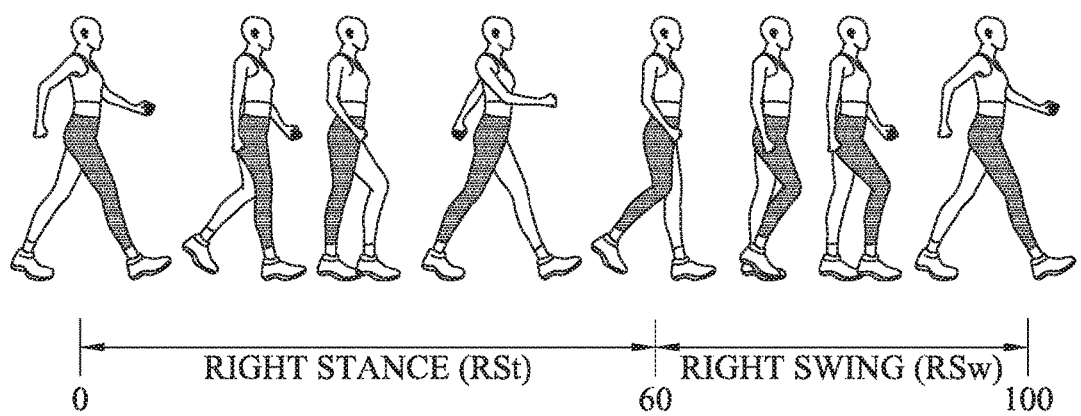
FIG. 13 illustrates gait states according to at least one example embodiment.

FIG. 13 illustrates gait states according to at least one example embodiment.

Gait states of one of legs of a user with respect to a gait may be predefined. For example, the gait states may include a stance and a swing. Gait states of a left leg may include a left stance (LSt) and a left swing (LSw). Gait states of a right leg may include a right stance (RSt) and a right swing (RSw).

In an FSM, a gait cycle may be mapped with respect to a gait state in advance. For example, a gait cycle 0% may mapped to a point in time at which a stance is started, a gait cycle 60% may be mapped to a point in time at which a swing is started, and a gait cycle 100% may be mapped to a point in time immediately before a stance is started.

Figure 14:
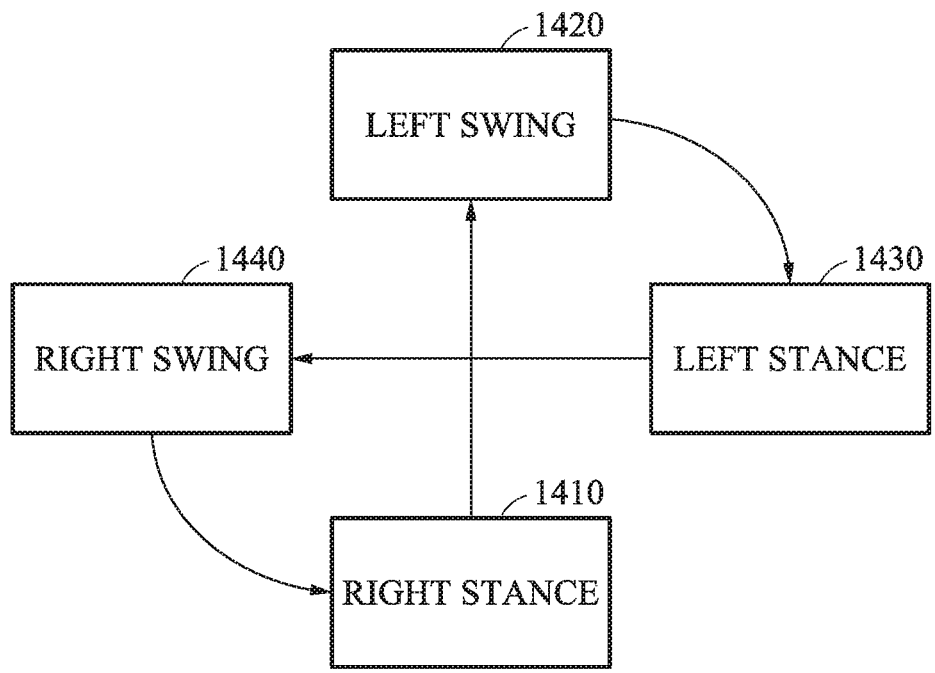
FIG. 14 illustrates a transition among gait states according to at least one example embodiment.

FIG. 14 illustrates a transition among gait states according to at least one example embodiment.

According to a general gait mechanism, a gait state at a start of a gait may vary. However, a transition among gait states may occur in an order of a right stance 1410, a left swing 1420, a left stance 1430, and a right swing 1440. After the right swing 1440 is performed, the right stance 1410 may be re-performed.

Figure 15:
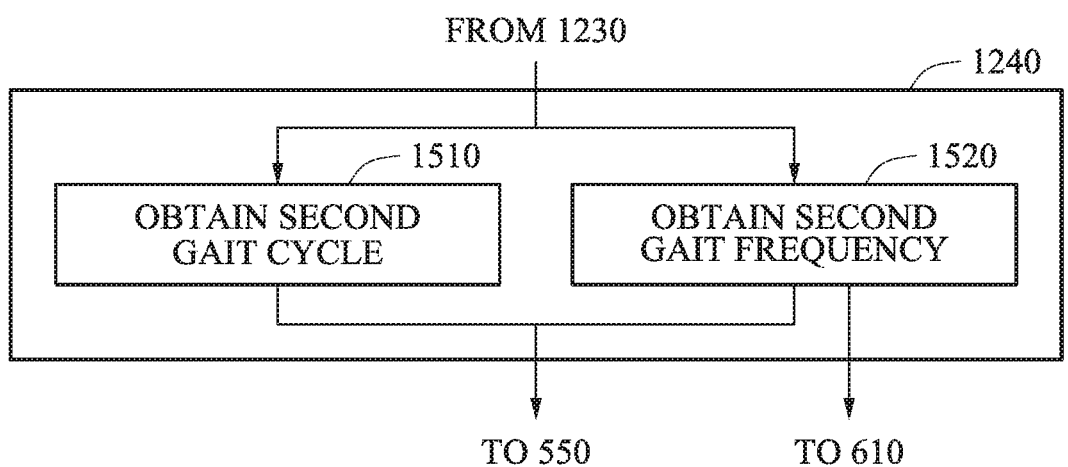
FIG. 15 is a flowchart illustrating a method of obtaining a second gait cycle and a second gait frequency according to at least one example embodiment.

FIG. 15 is a flowchart illustrating a method of obtaining a second gait cycle and a second gait frequency according to at least one example embodiment.

Referring to FIG. 15, operation 1240 of FIG. 12 may include operations 1510 and 1520.

In operation 1510, the processor 312 of FIG. 3 may obtain a second gait cycle as a gait parameter.

The processor 312 may define a value preset with respect to a current gait state as a value of the second gait cycle. For example, when the current gait state corresponds to a right swing, a gait cycle 60% preset with respect to the right swing may be defined as the value of the second gait cycle.

In operation 1520, the processor 312 may calculate a second gait frequency as the gait parameter.

The processor 312 may calculate the second gait frequency based on a period of a transition. For example, the second gait frequency may be calculated by calculating a period that it takes for a gait state of a left swing to be re-performed.

When a desired (or, alternatively, a predetermined) number of gait states corresponds to "4", a sum of durations of recent four gait states may be a time with respect to a single stride. An inverse number of the sum may be the second gait frequency.

The processor 312 may calculate the second gait frequency with respect to each gait state, and set a gait frequency corresponding to a current gait state as the second gait frequency each time the transition among the gait states occurs.

FIG. 15 illustrates that operation 550 of FIG. 5 is performed after operations 1510 and 1520 are performed. However, operation 530 of FIG. 5 may be performed after operations 1510 and 1520 are performed.

In operation 530, a gait cycle may be calculated based on the second gait cycle obtained in operation 1510 and the second gait frequency obtained in operation 1520.

The processor 312 may replace the value of the second gait cycle with a value of a first gait cycle. When the value of the second gait cycle is replaced with the value of the first gait cycle, an error in phase estimation that may occur in an early stage of a gait may be reduced.

In another example, the processor 312 may use the second gait frequency as a reference value to perform operation 610. When the second gait frequency is used as the reference value, an amount of time to be used to obtain a gait frequency may be reduced. For example, the processor 312 may set the second gait frequency directly as the gait frequency.

Figure 16:
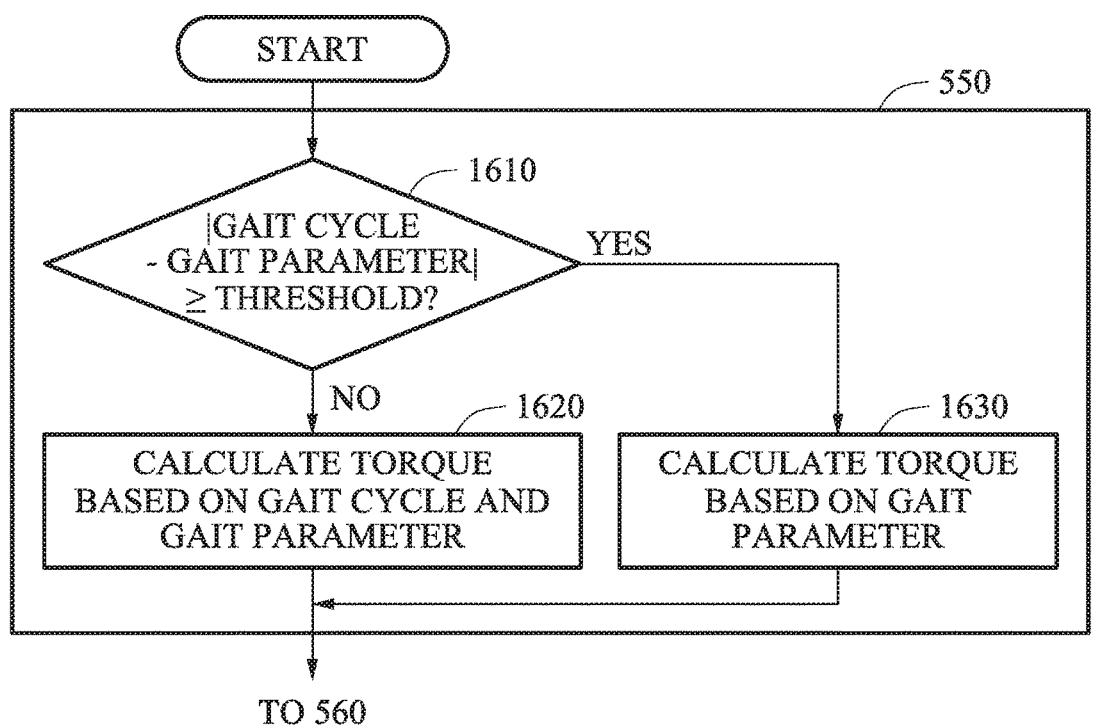
FIG. 16 is a flowchart illustrating a method of calculating a torque according to at least one example embodiment.

FIG. 16 is a flowchart illustrating a method of calculating a torque according to at least one example embodiment.

Referring to FIG. 16, operation 550 of FIG. 5 may include operations 1610 through 1630.

In operation 1610, the processor 312 of FIG. 3 may verify whether a difference between an obtained gait cycle and a gait parameter is greater than or equal to a threshold. For example, the gait parameter may be a second gait cycle. In some example embodiments, the threshold may be 10%.

Operation 1620 may be performed in response to a verification that the difference between the obtained gait cycle and the gait parameter is less than the preset threshold.

In operation 1620, the processor 312 may calculate a torque based on the gait cycle and the gait parameter.

The processor 312 may correct the obtained gait cycle using the gait parameter as a reference value. For example, the processor 312 may correct the gait cycle using the PSAO described above.

The processor 312 may calculate or obtain an output torque corresponding to the corrected gait cycle.

The processor 312 may perform Operation 1630 in response to a verification that the difference between the obtained gait cycle and the gait parameter is greater than or equal to the preset threshold.

In operation 1630, the processor 312 may calculate the torque based on only the gait parameter.

The processor 312 may set a value of the gait parameter as a value of the gait cycle. For example, the processor 312 may change the gait cycle obtained using the PSAO to the gait parameter, for example, the second gait cycle, obtained using an FSM.

The processor 312 may calculate or obtain an output torque corresponding to the set gait cycle.

Figure 17:
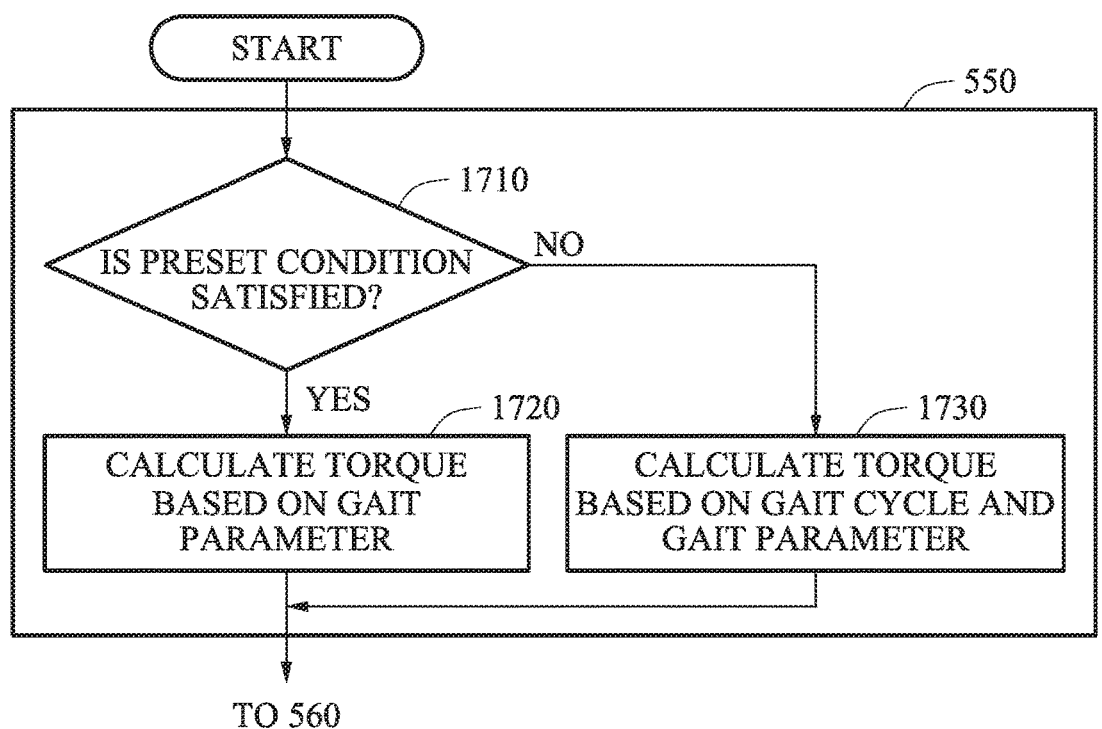
FIG. 17 is a flowchart illustrating a method of calculating a torque according to at least one example embodiment.

FIG. 17 is a flowchart illustrating a method of calculating a torque according to at least one example embodiment.

Referring to FIG. 17, operation 550 of FIG. 5 may include operations 1710 through 1730.

In operation 1710, the processor 312 of FIG. 3 may verify whether a preset condition is satisfied.

The preset condition may be a motion initial verification condition. For example, the motion initial verification condition may be that a number of times one of the desired (or, alternatively the predetermined) number of gait states is determined to be the current gait state is less than a preset value. For example, the preset value may be "2". In detail, the motion initial verification condition may be that two or fewer strides are performed after a gait is started.

In response to a verification that the preset condition is satisfied, operation 1720 may be performed.

In operation 1720, the processor 312 may calculate a torque based on only the gait parameter. For example, the gait parameter may be a second gait cycle.

The processor 312 may calculate a torque corresponding to the second gait cycle.

In response to a verification that the preset condition is not satisfied, operation 1730 may be performed.

In operation 1730, the processor 312 may calculate the torque based on the gait cycle and the gait parameter.

The processor 312 may correct the gait cycle based on the gait parameter. The processor 312 may calculate a torque with respect to the corrected gait cycle.

Figure 18:
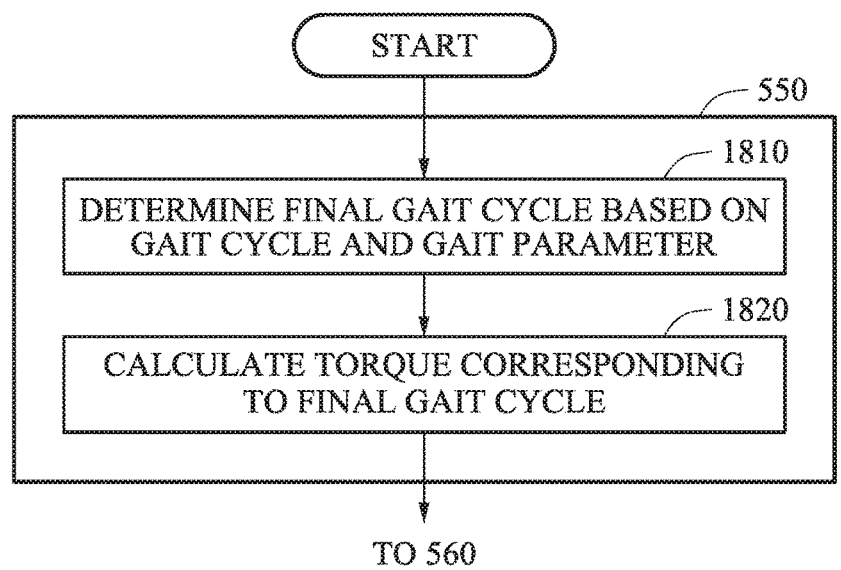
FIG. 18 is a flowchart illustrating a method of calculating a torque according to at least one example embodiment.

FIG. 18 is a flowchart illustrating a method of calculating a torque according to at least one example embodiment.

Referring to FIG. 18, operation 550 of FIG. 5 may include operations 1810 and 1820.

In operation 1810, the processor 312 of FIG. 3 may determine a final gait cycle based on a gait cycle and a gait parameter.

The processor 312 may calculate the final gait cycle by correcting the gait cycle based on the gait parameter.

In operation 1820, the processor 312 may calculate a torque corresponding to the final gait cycle. The calculated torque may be an output torque.

The processor 312 may calculate or obtain the output torque using a torque function corresponding to a reference trajectory. For example, the processor 312 may transform the torque function corresponding to the reference trajectory based on the final gait cycle, and calculate the output torque using the transformed torque function.

At least one reference trajectory with respect to a gait speed may be stored in a PSAO.

For example, when a user runs, in detail, when the gait speed is high, the reference trajectory may have a great change in a hip joint angle.

When the user walks, in detail, when the gait speed is low, the reference trajectory may have a modest change in the hip joint angle.

The output torque may be calculated based on assistance torque data preset to correspond to the corrected reference trajectory. The preset assistance torque data in which joint angles are matched to assistance torques, respectively, may be stored in the storage 313 of FIG. 3 in a form of a look-up table.

The processor 312 may search the corrected reference trajectory for a measured joint angle and an assistance torque matched to the joint angle. The processor 312 may determine a found assistance torque to be an assistance torque corresponding to a current gait cycle.

A plurality of items of assistance torque data may be preset to correspond to the corrected reference trajectory. For example, the preset assistance torque data may be assistance torque data classified by each gait speed of a user. The preset assistance torque data may be assistance torque data classified by a gradient of the ground. The preset assistance torque data may be assistance torque data classified by an age of a user. The preset assistance torque data may be assistance torque data classified by a gender of a user. The preset assistance torque data may be assistance torque data classified by a weight of a user.

Figure 19:
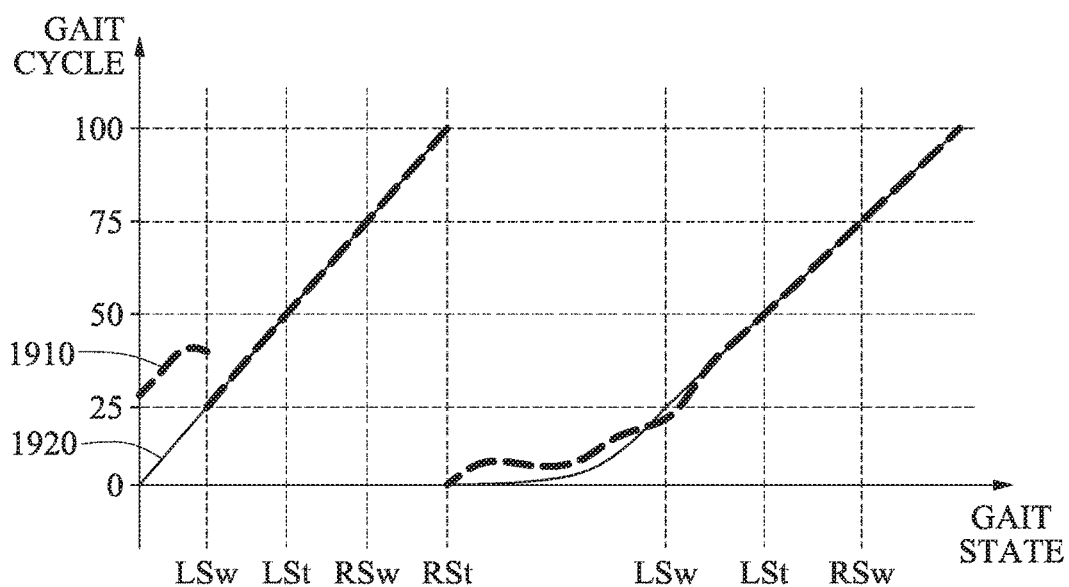
FIG. 19 illustrates results of a finally obtained gait cycle according to at least one example embodiment.

FIG. 19 illustrates results of a finally obtained gait cycle according to at least one example embodiment.

Referring to FIG. 19, a solid line 1920 indicates a gait cycle of a true value. The gait cycle of the true value may continuously increase.

For example, when a gait frequency is constant, the gait cycle of the true value may increase linearly. In FIG. 19, the gait cycle of the true value between a first left swing and a first right stance increases linearly.

Conversely, when the gait frequency is not constant, the gait cycle of the true value may increase non-linearly. In FIG. 19, the gait cycle of the true value between the first right stance and a second left swing increases non-linearly.

A broken line 1910 indicates an obtained gait cycle.

When a gait cycle is obtained using only a PSAO, a difference between the gait cycle obtained in an early stage of a gait and the gait cycle of the true value may be considerable.

When a first transition occurs, for example, when a left swing LSw occurs, the processor 312 of FIG. 3 may set a second gait cycle measured by an FSM as the gait cycle. After the transition occurred, the obtained gait cycle follows the gait cycle of the true value.

When a gait speed changes, the processor 312 may obtain a gait cycle based on a gait parameter obtained from the FSM. In FIG. 19, a gait cycle obtained in a period between a first right stance (Rst) and a second left swing (LSw) follows the non-linear gait cycle of the true value.

Figure 20:
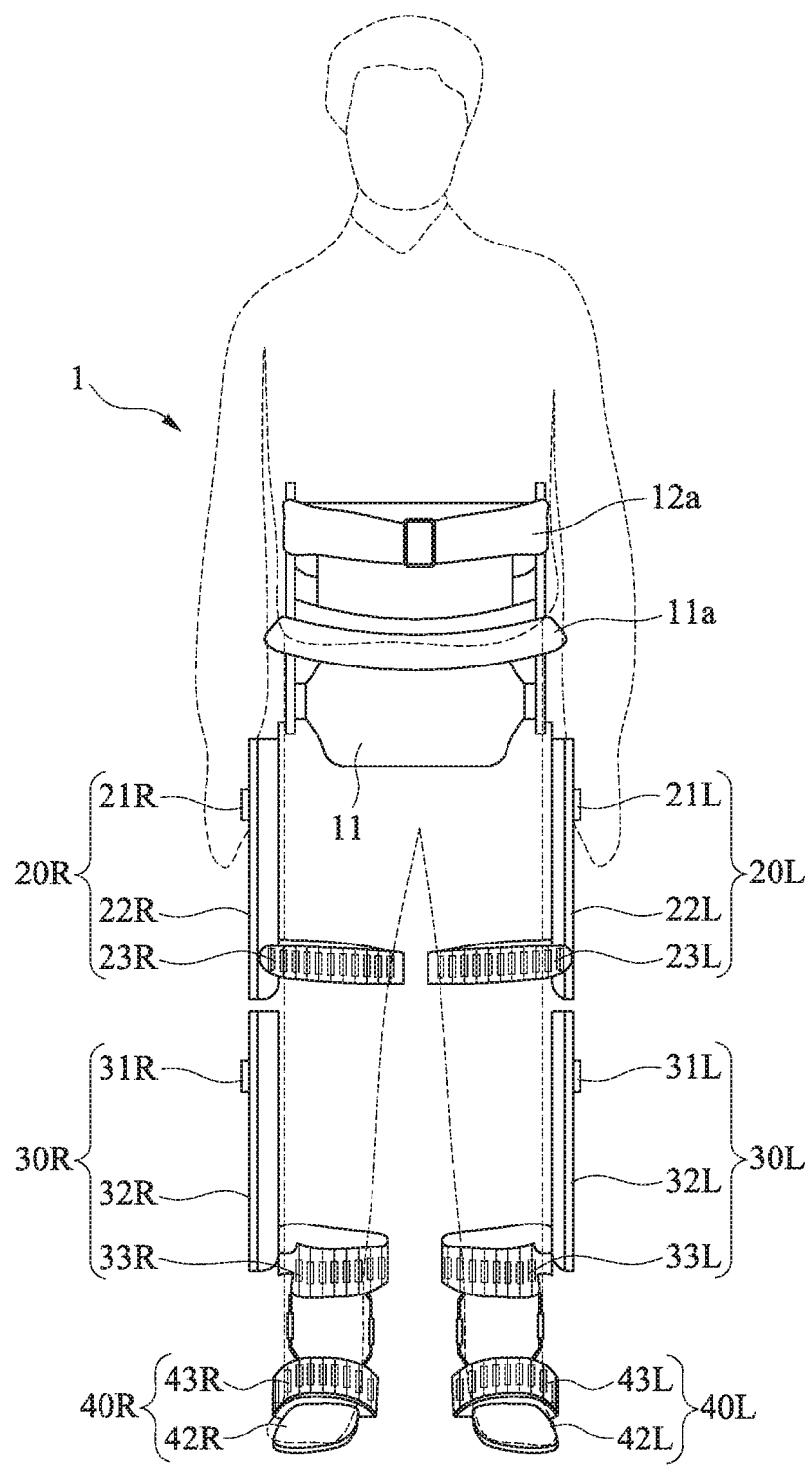
FIGS. 20 through 22 illustrate a walking assistance device according to at least one example embodiment.
Figure 21:
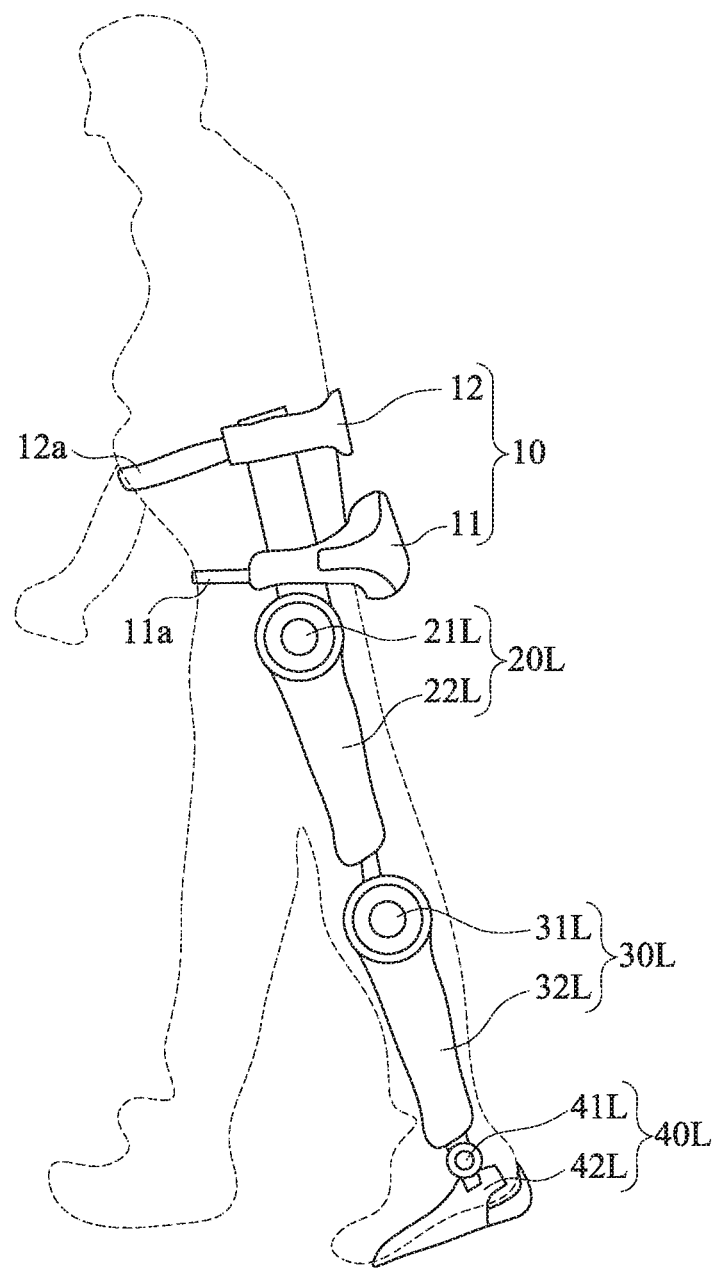
Figure 22:
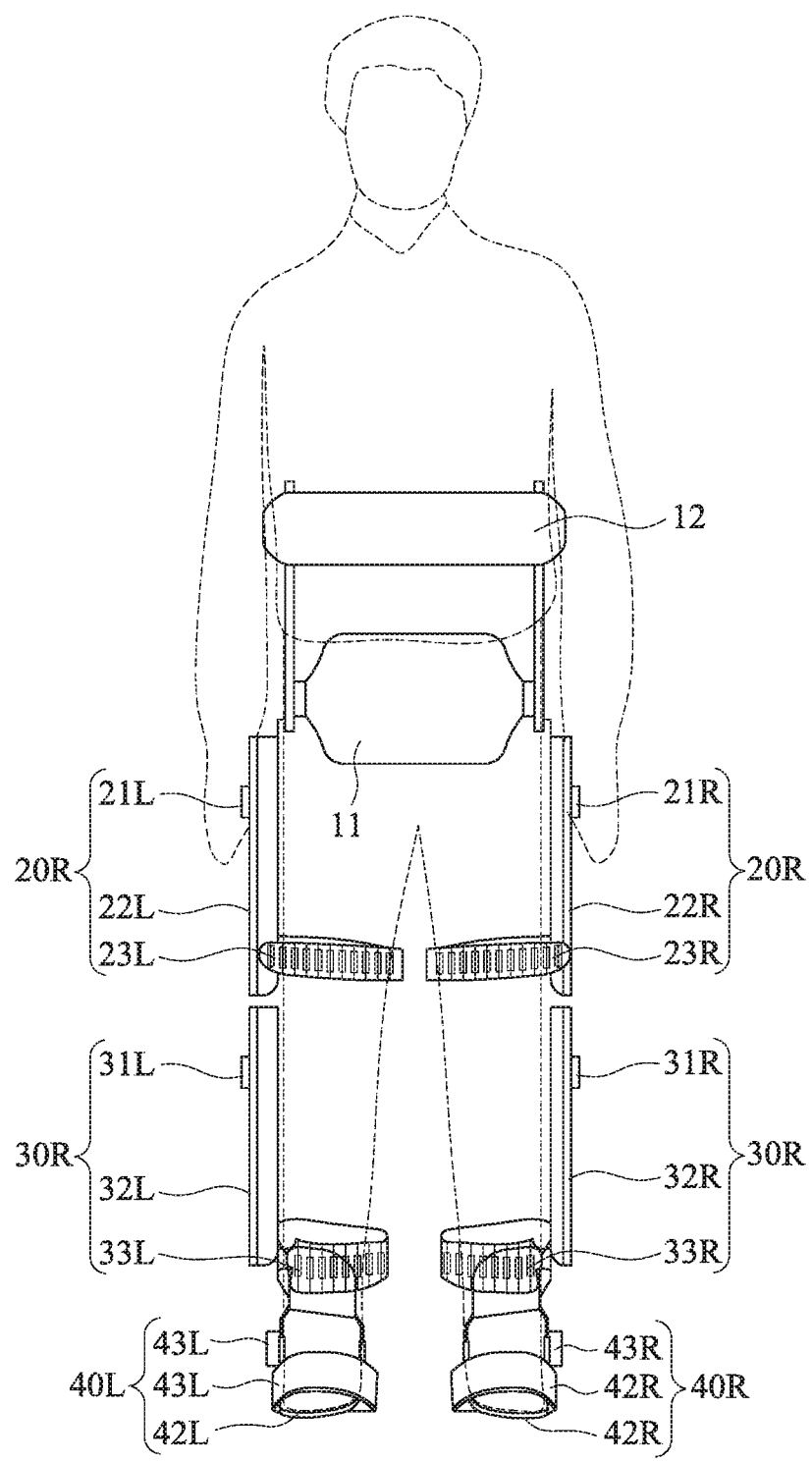

FIGS. 20 through 22 illustrate a walking assistance device according to at least one example embodiment.

Referring to FIGS. 20 through 22, another example of a wearable walking assistance device 1 that may be worn on a human body is illustrated. FIG. 20 is a front view of the walking assistance device 1, FIG. 21 is a side view of the walking assistance device 1, and FIG. 22 is a rear view of the walking assistance device 1.

The walking assistance device 1 may include the driving portion 110, the sensor portion 120, the IMU sensor 130, and the controller 140 of FIG. 1.

As shown in FIGS. 20 through 22, the walking assistance device 1 may have an exoskeleton structure to be worn on a left leg and a right leg of a user. The user may perform motions, such as an extension, a flexion, an adduction, and an abduction, for example, while wearing the walking assistance device 1. The extension motion may be a motion of extending a joint, and the flexion motion may be a motion of bending a joint. The adduction motion may be a motion of bringing a leg close to a central axis of a body. The abduction motion may be a motion of stretching a leg away from a central axis of a body.

Referring to FIGS. 20 through 22, the walking assistance device 1 may include a main body 10, and device portions 20R, 20L, 30R, 30L, 40R, and 40L.

The main body 10 may include a housing 11. A variety of components may be embedded in the housing 11. The components embedded in the housing 11 may include a Central Processing Unit (CPU), a printed circuit board (PCB), various types of storage devices, and a power source. The main body 10 may include the controller 140 of FIG. 1. The controller 140 may include the CPU and the PCB.

The CPU may be a microprocessor. The microprocessor may be a component on a silicon chip including an arithmetic logic unit, a register, a program counter, a command decoder, and/or a control circuit. The CPU may select a control mode suitable for a gait task, and generate a control signal to control operations of the device portions 20R, 20L, 30R, 30L, 40R, and 40L based on the selected control mode.

The PCB may be a board on which a circuit is printed. A CPU and/or various storage devices may be provided on the PCB. The PCB may be fixed to an inner side surface of the housing 11.

Various types of storage devices may be embedded in the housing 11. The storage devices may include a magnetic disk storage device that stores data by magnetizing a magnetic disk surface, and a semiconductor memory device that stores data using various types of memory semiconductors.

The power source embedded in the housing 11 may supply power to the variety of components embedded in the housing 11 or the device portions 20R, 20L, 30R, 30L, 40R, and 40L.

The main body 10 may further include a waist supporter 12 to support a waist of a user. The waist supporter 12 may have a shape of a curved plate to support the waist of the user.

The main body 10 may further include a fixing portion 11a to fix the housing 11 to a hip portion of the user, and a fixing portion 12a to fix the waist supporter 12 to the waist of the user. The fixing portions 11a and 12a may be implemented using one of bands, belts, and straps having elasticity.

The main body 10 may include the IMU sensor 130. For example, the IMU sensor 130 may be provided in an external portion or an internal portion of the housing 11. The IMU sensor 130 may be installed on the PCB provided in the internal portion of the housing 11. The IMU sensor 130 may measure an acceleration and an angular velocity.

The devices portions 20R, 20L, 30R, 30L, 40R, and 40L may also be referred to as first structure portions 20R and 20L, second structure portions 30R and 30L, and third structure portions 40R, and 40L.

The first structure portions 20R and 20L may assist motions of femoral portions and hip joints of the user during a gait motion. The first structure portions 20R and 20L may include first driving portions 21R and 21L, first supporters 22R and 22L, and first fixing portions 23R and 23L.

The driving portion 110 may include the first driving portions 21R and 21L. Thus, descriptions of the driving portion 110 provided with reference to FIGS. 1 through 19 may substitute for descriptions of the first driving portions 21R and 21L.

The first driving portions 21R and 21L may be disposed on hip joints of the first structure portions 20R and 20L, and generate torques at various magnitudes in desired (or, alternatively, predetermined) directions. The torques generated by the first driving portions 21R and 21L may be applied to the first supporters 22R and 22L. The first driving portions 21R and 21L may be set to rotate within motion ranges of hip joints of a human body.

The first driving portions 21R and 21L may be driven based on a control signal provided from the main body 10. The first driving portions 21R and 21L may be implemented using one of motors, vacuum pumps, and hydraulic pumps. However, the example embodiment is not limited thereto.

Joint angle sensors may be provided in the vicinity of the first driving portions 21R and 21L. The joint angle sensors may detect angles at which the first driving portions 21R and 21L rotate on rotation axes. The sensor portion 120 may include the joint angle sensors.

The first supporters 22R and 22L may be physically connected to the first driving portions 21R and 21L. The first supporters 22R and 22L may rotate in predetermined directions by the torques generated by the first driving portions 21R and 21L.

The first supporters 22R and 22L may be implemented in various shapes. In an example, the first supporters 22R and 22L may be implemented in a shape in which a plurality of segments is connected to each other. In this example, a joint may be provided between segments, and the first supporters 22R and 22L may be bent by the joint within a predetermined range. In another example, the first supporters 22R and 22L may be implemented in a shape of a rod. In this example, the first supporters 22R and 22L may be implemented using a flexible material to be bent within a predetermined range.

The first fixing portions 23R and 23L may be provided in the first supporters 22R and 22L. The first fixing portions 23R and 23L may fix the first supporters 22R and 22L to the femoral portions of the user.

FIGS. 20 through 22 illustrate a case in which the first fixing portions 23R and 23L fix the first supporters 22R and 22L to outer sides of the femoral portions of the user. When the first supporters 22R and 22L rotate in response to the first driving portions 21R and 21L being driven, the femoral portions to which the first supporters 22R and 22L are fixed may also rotate in directions identical to rotation directions of the first supporters 22R and 22L.

The first fixing portions 23R and 23L may be implemented using one of bands, belts, and straps having elasticity, or may be implemented using a metallic material. FIG. 20 illustrates a case in which the first fixing portions 23R and 23L are chains.

The second structure portions 30R and 30L may assist motions of sural portions and knee joints of the user during the gait motion. The second structure portions 30R and 30L may include second driving portions 31R and 31L, second supporters 32R and 32L, and second fixing portions 33R and 33L.

The second driving portions 31R and 31L may be disposed on knee joints of the second structure portions 30R and 30L, and generate torques at various magnitudes in predetermined directions. The torques generated by the second driving portions 31R and 31L may be applied to the second supporters 22R and 22L. The second driving portions 31R and 31L may be set to rotate within motion ranges of knee joints of a human body.

The driving portion 110 may include the second driving portions 31R and 31L. Thus, descriptions related to the hip joints provided with reference to FIGS. 1 through 19 may be similarly applicable to descriptions related to the knee joints.

The second driving portions 31R and 31L may be driven based on the control signal provided from the main body 10. The second driving portions 31R and 31L may be implemented using one of motors, vacuum pumps, and hydraulic pumps. However, the example embodiment is not limited thereto.

Joint angle sensors may be provided in the vicinity of the second driving portions 31R and 31L. The joint angle sensors may detect angles at which the second driving portions 31R and 31L rotate on rotation axes. The sensor portion 120 may include the joint angle sensors.

The second supporters 32R and 32L may be physically connected to the second driving portions 31R and 31L. The second supporters 32R and 32L may rotate in predetermined directions by the torques generated by the second driving portions 31R and 31L.

The second fixing portions 33R and 33L may be provided in the second supporters 32R and 32L. The second fixing portions 33R and 33L may fix the second supporters 32R and 32L to the sural portions of the user. FIGS. 20 through 22 illustrate a case in which the second fixing portions 33R and 33L fix the second supporters 32R and 32L to outer sides of the sural portions of the user. When the second supporters 32R and 32L rotate in response to the second driving portions 31R and 31L being driven, the sural portions to which the second supporters 32R and 32L are fixed may also rotate in directions identical to rotation directions of the second supporters 32R and 32L.

The second fixing portions 33R and 33L may be implemented using one of bands, belts, and straps having elasticity, or may be implemented using a metallic material.

The third structure portions 40R and 40L may assist motions of ankle joints and related muscles of the user during the gait motion. The third structure portions 40R and 40L may include third driving portions 41R and 41L, foot rests 42R and 42L, and third fixing portions 43R and 43L.

The driving portion 110 may include the third driving portions 41R and 41L. Thus, descriptions related to the hip joints provided with reference to FIGS. 1 through 19 may be similarly applicable to descriptions related to the ankle joints.

The third driving portions 41R and 41L may be disposed on ankle joints of the third structure portions 40R and 40L, and driven based on the control signal provided from the main body 10. Similar to the first driving portions 21R and 21L or the second driving portions 31R and 31L, the third driving portions 41R and 41L may be implemented using motors.

Joint angle sensors may be provided in the vicinity of the third driving portions 41R and 41L. The joint angle sensors may detect angles at which the third driving portions 41R and 41L rotate on rotation axes. The sensor portion 120 may include the joint angle sensors.

The foot rests 42R and 42L may be provided at positions corresponding to soles of the user, and physically connected to the third driving portions 41R and 41L.

Pressure sensors may be provided in the foot rests 42R and 42L to sense a weight of the user. Sensing results of the pressure sensors may be used to verify whether the user is wearing the walking assistance device 1, whether the user is standing, and whether feet of the user are in contact with the ground.

The third fixing portions 43R and 43L may be provided in the foot rests 42R and 42L. The third fixing portions 43R and 43L may fix the feet of the user to foot rests 42R and 42L.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of calculating an output torque of a walking assistance device via a controller connected to one or more sensors, the method comprising:
    sensing, via signals from the one or more sensors, a joint angle associated with a joint of a user;
    determining a gait cycle by applying the joint angle to an adaptive oscillator (AO);
    determining a gait parameter from observing a recurring target event;
    calculating the output torque based on the gait cycle and the gait parameter, the calculating including,
        correcting the gait cycle using the gait parameter as a reference value to generate a corrected gait cycle; and
        calculating the output torque corresponding to the corrected gait cycle, and
        instructing a driver to apply the output torque to a support of the walking assistance device associated with the joint of the user.

2. The method of claim 1, wherein the determining the gait cycle comprises:
    calculating a first gait frequency based on the joint angle; and
    determining the gait cycle based on the first gait frequency.

3. The method of claim 1, wherein the determining the gait parameter comprises:
    determining a current one of a plurality of gait states based on a previous one of the plurality of gait states and the joint angle;
    determining if a transition among the plurality of gait states occurred based on the previous one of the plurality of gait states and the current one of the plurality of gait states; and
    determining the gait parameter in response to a determination that the transition occurred.

4. The method of claim 3, wherein
    the determining the gait parameter further includes determining a second gait cycle as the gait parameter, and
    the calculating the output torque includes calculating the output torque based on the gait cycle and the second gait cycle.

5. The method of claim 4, wherein the determining the second gait cycle comprises:
defining a value preset with respect to the current one of the gait states as a value of the second gait cycle.

6. The method of claim 3, wherein
the determining the gait parameter includes calculating a second gait frequency as the gait parameter, and
the calculating the output torque includes calculating the output torque based on the gait cycle and the second gait frequency.

7. The method of claim 6, wherein the calculating of the second gait frequency comprises:
calculating the second gait frequency based on a period of the transition.

8. The method of claim 3, wherein the determining the current one of the gait states comprises:
determining a gait state corresponding to the joint angle, among the gait states with respect to the joint angle, to be the current one of the gait states.

9. The method of claim 1, wherein the calculating the output torque comprises:
determining whether a difference between the gait cycle and the gait parameter is greater than or equal to a threshold; and
calculating the output torque based on the gait parameter in response to a determination that the difference is greater than or equal to the threshold.

10. The method of claim 1, wherein the calculating the output torque comprises:
determining whether a difference between the gait cycle and the gait parameter is greater than or equal to a threshold; and
calculating the output torque based on the gait cycle and the gait parameter, if the difference is less than the threshold.

11. The method of claim 1, wherein the calculating the output torque comprises:
determining whether a condition is satisfied; and
calculating the output torque based on the gait parameter, if the condition is satisfied.

12. The method of claim 11, wherein the condition is an initial stage of walking.

13. The method of claim 12, wherein the condition is determined as the initial stage of walking when a current one of a plurality of gait states has been determined less than a set number of times.

14. The method of claim 1, wherein the calculating the output torque comprises:
determining a final gait cycle based on the gait cycle and the gait parameter; and
calculating the output torque corresponding to the final gait cycle.

15. The method of claim 1, wherein the joint angle is an angle of at least one of a hip joint, a knee joint, and an ankle joint.

16. The method of claim 1, wherein the recurring target event is an event of joint velocity changing to positive from negative or changing in an opposite direction.

17. The method of claim 1, wherein the recurring target event is an event of a foot contact sensor becoming 'ON' from 'OFF'.

18. The method of claim 1, wherein the recurring target event is an event of a visiting a target gait state.

19. A torque calculating apparatus comprising:
one or more sensors configured to sense a joint angle associated with a joint of a user;
a receiver configured to receive a measurement of the joint angle; and
a processor configured to,
determine a gait cycle by applying the joint angle to an adaptive oscillator (AO);
determine a gait parameter from observing a recurring target event;
calculate output torque based on the gait cycle and the gait parameter by,
correcting the gait cycle using the gait parameter as a reference value to generate a corrected gait cycle; and
calculating the output torque corresponding to the corrected gait cycle, and
instruct a driver to apply the output torque to a support of a walking assistance device associated with the joint of the user.

20. A torque calculating method via a controller connected to one or more sensors, the method comprising:
sensing, via signals from the one or more sensors, a joint angle associated with a joint of a user;
obtaining a first gait cycle based on a measured joint angle using an adaptive oscillator (AO);
obtaining a second gait cycle from observing a recurring target event;
calculating a final gait cycle based on the first gait cycle and the second gait cycle when a transition occurs;
calculating a torque corresponding to the final gait cycle; and
instructing a driver to apply the torque to a support of a walking assistance device associated with the joint of the user.

* * * * *